(12) United States Patent
Arthur et al.

(10) Patent No.: US 10,363,509 B2
(45) Date of Patent: Jul. 30, 2019

(54) AIR FILTER CONDITION SENSING

(71) Applicant: 3M INNOVATIVE PROPERTIES COMPANY, St. Paul, MN (US)

(72) Inventors: Jonathan B. Arthur, Hudson, WI (US); Karl W. Bloedorn, Saint Paul, MN (US); Jayant Chakravarty, Woodbury, MN (US); Gene B. Portelli, Lake Elmo, MN (US); Dennis M. Glass, Cottage Grove, MN (US); Michael A. Meis, Stillwater, MN (US); Lyle L. Luppes, Rosemount, MN (US); Daniel W. Hennen, Cottage Grove, MN (US); Douglas D. Fletcher, Woodbury, MN (US); Eric O. Hemberg, Shatin (HK); Oscar M. Hemberg, Dalaro (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/876,742

(22) Filed: Jan. 22, 2018

(65) Prior Publication Data
US 2018/0140989 A1    May 24, 2018

Related U.S. Application Data

(63) Continuation of application No. PCT/US2017/045508, filed on Aug. 4, 2017.
(Continued)

(51) Int. Cl.
*B01D 46/00* (2006.01)
*G01L 19/08* (2006.01)
*H04W 4/38* (2018.01)
*B01D 46/10* (2006.01)
*B01D 46/44* (2006.01)
*B01D 46/52* (2006.01)

(52) U.S. Cl.
CPC ......... *B01D 46/0086* (2013.01); *B01D 46/10* (2013.01); *B01D 46/446* (2013.01); *B01D 46/521* (2013.01); *G01L 19/086* (2013.01); *H04W 4/38* (2018.02)

(58) Field of Classification Search
CPC ..... B01D 46/0086; H04W 4/38; G01L 19/086
See application file for complete search history.

(56) References Cited

U.S. PATENT DOCUMENTS

| 4,316,365 A | 2/1982 | Mueller et al. |
| 5,001,463 A | 3/1991 | Hamburger |

(Continued)

FOREIGN PATENT DOCUMENTS

WO    WO 2011-29574    3/2011

OTHER PUBLICATIONS

International Search Report, PCT/US2017/045508/, dated Oct. 18, 2017, 3 pages.

*Primary Examiner* — Sisay Yacob
(74) *Attorney, Agent, or Firm* — Kevin Weber

(57) ABSTRACT

An air filter includes filter media, a sensor, and circuitry coupled to the sensor, the circuitry configured to receive data from the sensor representative of the condition of the filter media and wirelessly transmit such data. The data may be received by a device with a display to use the information to present an indication of the filter media condition to a user.

21 Claims, 24 Drawing Sheets

Related U.S. Application Data

(60) Provisional application No. 62/374,040, filed on Aug. 12, 2016, provisional application No. 62/372,156, filed on Aug. 8, 2016.

(56) References Cited

U.S. PATENT DOCUMENTS

| | | |
|---|---|---|
| 6,894,620 B2 | 5/2005 | Reinhardt et al. |
| 6,993,414 B2 | 1/2006 | Shah |
| 7,012,685 B1 | 3/2006 | Wilson |
| 7,174,273 B2 | 2/2007 | Goldberg |
| 7,244,294 B2 | 7/2007 | Kates |
| 7,261,762 B2 | 8/2007 | Kang et al. |
| 8,029,608 B1 | 10/2011 | Breslin |
| 8,613,792 B2 | 12/2013 | Ragland et al. |
| 8,623,117 B2 | 1/2014 | Zavodny et al. |
| 8,626,456 B2 | 1/2014 | Moore et al. |
| 8,704,672 B2 | 4/2014 | Hoglund et al. |
| 9,120,043 B2 | 9/2015 | Johansson et al. |
| 9,200,995 B2 | 12/2015 | Ahola et al. |
| 9,207,727 B2 | 12/2015 | Balogh et al. |
| 9,481,004 B2 * | 11/2016 | Vickers .............. B01D 46/0001 |
| 9,517,429 B2 | 12/2016 | Beier |
| 9,552,715 B2 | 1/2017 | Breslin |
| 9,593,861 B1 * | 3/2017 | Burnett .................... F24F 11/30 |
| 2002/0104967 A1 * | 8/2002 | Kouznetsov ....... G01N 21/3504 250/339.13 |
| 2005/0150304 A1 * | 7/2005 | Gustafson ............. G01L 9/0089 73/754 |
| 2006/0100796 A1 * | 5/2006 | Fraden ...................... A47L 9/19 702/45 |
| 2007/0013534 A1 * | 1/2007 | DiMaggio ................ G08B 5/36 340/607 |
| 2008/0198896 A1 | 8/2008 | Nair |
| 2009/0165644 A1 | 7/2009 | Campbell |
| 2011/0185895 A1 | 8/2011 | Freen |
| 2012/0318073 A1 * | 12/2012 | Zavodny ............ B01D 46/0086 73/862.581 |
| 2014/0278681 A1 | 9/2014 | Cox et al. |
| 2016/0174146 A1 | 6/2016 | Wang et al. |
| 2016/0184755 A1 | 6/2016 | Chen et al. |
| 2017/0189844 A1 | 7/2017 | McLeod et al. |
| 2017/0320004 A1 | 11/2017 | Allegorico et al. |
| 2017/0361259 A1 | 12/2017 | Fox et al. |
| 2018/0012479 A1 | 1/2018 | Seaton et al. |

* cited by examiner

| Air speed (fpm) | Sensor dP (mbar) | Daffy dP (in H2O) | Calc dP Sensor (in H2O) | |
|---|---|---|---|---|
| 300 | 0.57 | 0.21 | 0.229 | A |
| 300 | 0.53 | 0.21 | 0.213 | A |
| 400 | 0.84 | 0.34 | 0.338 | B |
| 400 | 0.91 | 0.35 | 0.366 | B |
| 400 | 0.88 | 0.35 | 0.354 | B |
| 500 | 1.31 | 0.525 | 0.526 | C |
| 500 | 1.34 | 0.525 | 0.538 | C |

| HVAC mode | dP gauge(home) (inches H2O) | Sensor (mbar) | Sensor max. (mbar) | |
|---|---|---|---|---|
| Rheem Criterion | | | | |
| Fan ON | 0.51 | 1.07 | 1.09 | A |
| A/C ON | 0.46 | 0.91 | 1.11 | B |
| A/C + Fan ON | 0.47 | 0.85 | 1.11 | C |
| A/C Off, Fan ON | 0.51 | 1.03 | 1.11 | D |
| Off | 0 | 0.01 | 1.12 | E |

| | A | B | C | D | E | F | G | H |
|---|---|---|---|---|---|---|---|---|
| 1 | ip | pressure | eventTime | max_accel | max_accel | max_accel | serialNumber | experiment |
| 2 | 169.12.46. | 986.2437 | 6/23/2016 18:32 | 0.016753 | 0.013335 | 1.017678 | b827ebd59036 | cleanfilterrunning |
| 3 | 169.12.46. | 986.3792 | 6/23/2016 18:32 | 0.016753 | 0.012365 | 1.019384 | b827ebd59036 | cleanfilterrunning |
| 4 | 169.12.46. | 986.3931 | 6/23/2016 18:32 | 0.017481 | 0.012607 | 1.018165 | b827ebd59036 | cleanfilterrunning |
| 5 | 169.12.46. | 986.3867 | 6/23/2016 18:32 | 0.016753 | 0.013577 | 1.014266 | b827ebd59036 | cleanfilterrunning |
| 6 | 169.12.46. | 986.3877 | 6/23/2016 18:32 | 0.016753 | 0.015274 | 1.01646 | b827ebd59036 | cleanfilterrunning |
| 7 | 169.12.46. | 986.3875 | 6/23/2016 18:32 | 0.016753 | 0.014304 | 1.019384 | b827ebd59036 | cleanfilterrunning |
| 8 | 169.12.46. | 986.397 | 6/23/2016 18:32 | 0.017238 | 0.014547 | 1.019628 | b827ebd59036 | cleanfilterrunning |
| 9 | 169.12.46. | 986.4229 | 6/23/2016 18:32 | 0.017481 | 0.013335 | 1.019628 | b827ebd59036 | cleanfilterrunning |
| 10 | 169.12.46. | 986.3958 | 6/23/2016 18:32 | 0.017238 | 0.013577 | 1.015241 | b827ebd59036 | cleanfilterrunning |

AIR FILTER CONDITION SENSING

CROSS REFERENCE TO RELATED APPLICATIONS

This application is a continuation application of PCT application PCT/US2017/045508, filed Aug. 4, 2017, which claims the benefit of U.S. Provisional Application No. 62/374,040, filed Aug. 12, 2016, and U.S. Provisional Application 62/372,156, filed Aug. 8, 2016, the entire content of which is incorporated herein by reference.

BACKGROUND

An air filter may be included in furnaces and stand-alone air purifiers. Air is drawn through the filter, and the filter traps particles, preventing them from proceeding through ducts to environmental spaces that are being heated, cooled, or otherwise conditioned.

In-home furnace air filters become ineffective or blocked over time and need to be replaced to minimize wear on furnace fan motors as well as to maintain air purification effectiveness and maintain adequate airflow. Traditional filter obstruction is defined by the difference in pressure before the filter and after the filter in respect to airflow. An increase in the difference in pressure is indicative of the filter becoming more blocked and needing replacement.

SUMMARY

An air filter includes filter media, a sensor, and circuitry coupled to the sensor, the circuitry configured to receive data from the sensor representative of the condition of the filter media and wirelessly transmit such data. The data may be received by a device or system with a display to use the information to present an indication of the filter media condition to a user.

DETAILED DESCRIPTION

Figure 1:
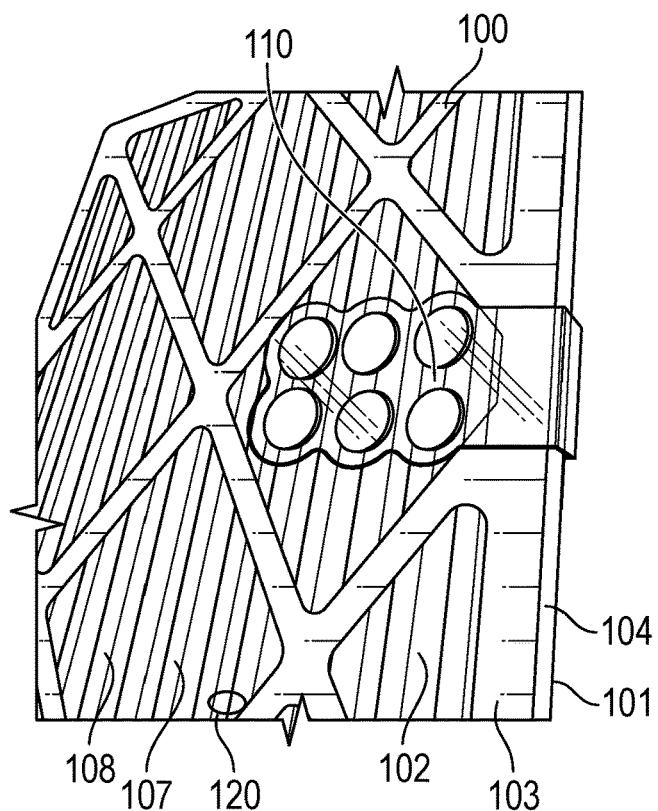
FIG. 1 is a photograph that includes a disposable air filter according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software in one embodiment. The software may consist of computer executable instructions stored on computer readable media or computer readable storage device such as one or more non-transitory memories or other type of hardware based storage devices, either local or networked. Further, such functions correspond to modules, which may be software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system, turning such computer system into a specifically programmed machine.

Embodiments are described to identify when an air filter should be replaced. The embodiments utilize sensors and analytics to determine if and when replacement is of the air filter is desired. A network connection may be used to communicate an indication of filter which should be replaced. The indication may be provided to a user via an application running on a mobile device that receives the indication via the network. Information may be transferred based on a network connection such as a Bluetooth Low Energy (BLE) connection direction between a sensor and analytics device associated with the filter, a Wi-Fi connection, ZigBee, or Zwave for example. An RFID based connection or other connection may be used to transfer information in further embodiments. The application may enable ordering of a replacement filter either automatically or responsive to a user selectable option provided on the mobile device by the application. The application may also provide for reading a bar code, QR code, or other information from a filter and use such information to control use of the sensor on only specified filters. The information may also be used to configure the sensors and/or application for an allowed pressure drop or airflow measurement parameter for a corresponding filter.

In one embodiment, a single pressure sensor, or a multitude of different sensors may be used to identify pressure obstruction of a filter. The single sensor may be positioned after the filter on the clean air side between the filter and fan side using a vacuum phenomenon created by the motor increasing effort as the filter becomes increasingly obstructed. In other words, the pressure drops while the fan is running, with the drop being greater as the filter becomes more obstructed. A threshold, such as a drop of 2 or more pascals while the fan is on compared to the fan being off, may be used to trigger customer notifications to replace the filter in one embodiment.

In one embodiment, the single pressure sensor provides pressure readings to analytics software executing on a processor. The processor and pressure sensor may be formed as an integrated unit. The integrated unit may also include networking capabilities. With the use of a single pressure sensor, the sensor may be calibrated by observing pressure with the fan on and the fan off. It may then be assumed that the pressure with the fan on is representative of the pressure difference between sides of the filter. Several examples of algorithms that utilize sensor data to generate notifications of filter obstruction are provided below.

Feedback may be provided to customers to communicate the effectiveness of air filtration filters as well as timing to replace and need to replace data. Previous concepts are susceptible to clogging by dirty air on the upstream side of the filter. Having to maintain two sensors also increases the sensor cost for the consumer. An affordable sensor can be provided to consumers to assist them in maintaining high air quality standards in their home through the appropriate servicing of their in-home furnace filter.

In a further embodiment, a differential pressure sensor may be coupled to the filter media with two openings on opposite sides of the filter media to communicate the pressure on each side to a differential pressure sensing element, such as a capacitor plate or piezoelectric element that flexes responsive to the difference in pressure. The sensing element may be located on one side with a first opening, with a tube with a second opening extending through the media to the other side of the media. The openings are disposed on either side of the differential pressure sensing element.

In further embodiments, parameters other than pressure may be measured or sensed and correlated with a filter condition indicative of a time to replace the filter. Such parameters include for example, load on the fan motor, airspeed, turbulence, particulates, optical clarity, vibration, thermoelectric sensor, strain gage indicative of bending, and others. In still further embodiments, data from one or more sensors may be fused or otherwise combined by the analytics software to generate the indication for filter replacement.

In some embodiments, the sensor and/or integrated sensor unit may attach to or be integrated with the filter media, or attached to a frame of the filter media. The frame may be a permanent refillable plastic filter frame. In some embodiments, the unit may be attached to filter media or a frame of the filter and reused by removing the unit and attaching the unit to a replacement filter, filter frame, or filter media. The unit may also be attached to a frame of a filter having replaceable filter media.

FIG. 1 is a photograph that includes a disposable air filter 100. The filter 100 may have a generally rectangular shape (which includes square shapes). Disposable filter 100 may comprise an upstream face 101 (facing away and not visible) and a downstream face 102, and may comprise a filter media 107 surrounded by an optional perimeter frame 103. The filter media 107 may be replaceable by removing the filter media from the frame and replacing the filter media with new or reconditioned filter media. In further embodiments, the filter media may be self-supporting without a frame if formed with sufficient structural integrity to maintain an effective shape for filtering air when subjected to airflow. In various embodiments, filter media 107 may be pleated so as to exhibit readily identifiable pleats 108, or, it may be unpleated. In one embodiment, a sensor 110, such as a pressure sensor is supported by the filter. The sensor 110 may include electronics to process and communicate sensor readings indicative of filter media condition. The sensor may be supported by a hanging structure as shown at 110 in FIG. 1 or affixed directly to the filter media or frame.

Perimeter frame 103 may often comprise sidewalls (e.g., top, bottom, left and right sidewalls) 104 that define terminal edges of the framed filter. Frame 103 may be made of any suitable material(s), e.g., paperboard or cardboard that may be folded to provide the various sidewalls. In some embodiments, the frame 103 may be made of an injection molded plastic material. In some embodiments, at least the downstream face 102 of filter 100 may comprise support members that extend at least partially across filter media 107 (in any direction). Such members may provide additional support, particularly on the downstream side of the filter media; and (particularly for pleated filter media), such members may assist in minimizing or ensuring consistency of deformation of the filter media in response to air pressure during operation of the room air purifier. In some embodiments such members may be strips of paperboard that may be connected to frame 103 at their terminal ends. In other embodiments such members may be lengths of adhesive strands. If the filter media is pleated, any such adhesive strands may be deposited either before or after the filter media is pleated.

Many different types of filter styles with various pleating options may be used. For example, mini-pleat designs may use wire affixed to the pleat tips on one or both sides of the filter. Micro pleat designs may use wire on one side of filter media where the wire is contoured to the pleating of the media to maintain the pleat shape. Flat panel filter media may use wire and/or polyolefin netting. Some filter designs may use polyolefin strands versus adhesive strands to maintain pleat spacing.

The filter media 107 (whether pleated or not) of a disposable air filter 100 may be comprised of nearly any material, in any configuration, that is capable of filtering moving air. Such media may include, but is not limited to, fibrous materials (e.g., nonwoven webs, fiberglass webs, and so on), honeycomb structures loaded with filter media and/or sorbent material, and so on. In particular embodiments, the filter media may include at least one layer that comprises at least some material that can be electrically or electrostatically charged to form an electret material. In particular embodiments, the filter media may be a multilayer media that comprises at least one layer that includes an electret material, and at least one layer that includes a sorbent material. In some embodiments filter media 107 may comprise at least one layer capable of HEPA filtration. Electrostatically charged media may enhance particulate capture. Electrically charged media may be used in electrostatic precipitators which have a current and ground wire and are typically washable.

If at least one layer of the filter media 107 is to exhibit sorbent functionality, any suitable sorbent(s), in any convenient physical form, may be included in such a layer. In particular embodiments, such a sorbent may be capable of capturing formaldehyde (formaldehyde is a very light gas which may not be captured by typical carbon filters. Many carbon filters capture much heavier gases such as urea, cooking odors, etc. These filters use activated carbons. To capture Formaldehyde and toluene gases, a treated (often acid treated) carbon may be used. In some embodiments, the sorbent includes at least some activated carbon. If desired, the activated carbon may be treated to enhance its ability to capture formaldehyde. Suitable treatments may e.g., provide the activated carbon with at least some amine functionality and/or at least some manganate functionality and/or at least some iodide functionality. Specific examples of treated activated carbons that may be suitable include those that have been treated with e.g., potassium permanganate, urea, urea/phosphoric acid, and/or potassium iodide. Other sorbents that may be potentially suitable e.g., for removing formaldehyde include e.g., treated zeolites and treated activated alumina. Such materials may be included e.g., along with treated activated carbon if desired.

The one or more sorbents may be provided in any usable form; for example as particles, which may be, e.g., powder, beads, flakes, whiskers, granules or agglomerates. The sorbent particle size may vary as desired. The sorbent particles may be incorporated into or onto a layer of filter media 107 in any desired fashion. For example, in various embodiments the sorbent particles may be physically entangled with fibers of a layer of filter media 107, may be adhesively bonded to such fibers, or some combination of both mechanisms may be used.

In one embodiment, disposable air filter 100 may include at least one RFID (radiofrequency identification) tag 120. In some embodiments, an RFID tag 120 may be mounted to any portion of a perimeter frame 103 of air filter 100. For example, an RFID tag 120 may be mounted to an interior major surface of a sidewall of the frame, or to an exterior or interior (i.e., visible or not visible) major surface of an upstream or downstream flange of the frame. In some embodiments, RFID tag 120 is mounted to (e.g., attached to, e.g., adhesively attached to) a major outward surface of a sidewall 104 of perimeter frame 103 of disposable air filter 100. RFID tag 120 may be any suitable RFID tag. In many embodiments, RFID tag 120 may be a passive tag, meaning that it does not include any kind of power source and is solely powered by the electromagnetic energy that is impinged upon it by the RFID reader. In some embodiments, RFID tag 120 may be a conventional RFID tag (operating e.g., at high, medium or low frequency) whose range is not particularly limited. In particular embodiments, RFID tag 120 may be a so-called Near Field Communication (NFC) tag, which will be recognized by the skilled person as being a particular type of RFID tag that operates (e.g., at 13.56 MHz) only over the range of a few (e.g., ten or less) centimeters. In some embodiments RFID tag 120 is a readable (only) tag; in other embodiments it may be a readable/writeable tag as discussed in detail later herein. In some embodiments, RFID tag 120 may conveniently be supplied with an adhesive backing so that RFID tag 120 can be quickly and easily installed onto a surface of a sidewall 104 of a frame of filter 100.

Figure 2:
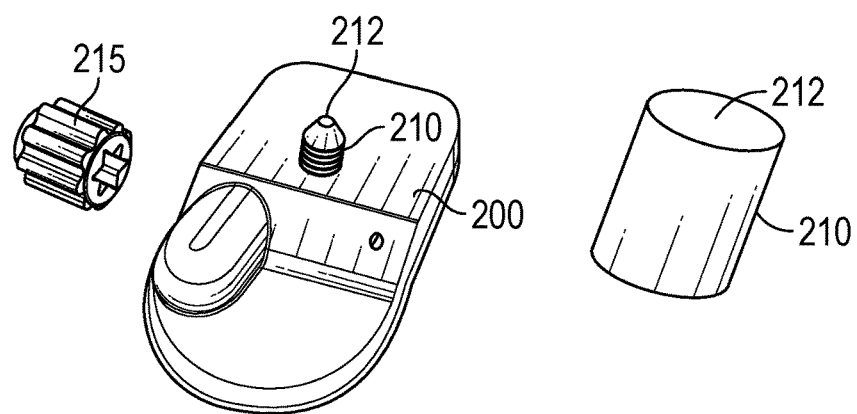
FIG. 2 is a photograph of a differential pressure sensor to couple to filter media according to an example embodiment.

In one embodiment, a single differential pressure sensor may be used and encased in a small plastic housing 200 as indicated in FIG. 2. The housing 200 may include one or more sensors to measure the differential pressure, processing electronics and Bluetooth Low Energy communication electronics. The pressure sensor(s) measures pressure drop of the filter to determine the filter's performance and when it should be replaced (i.e., the end of life for the filter).

In one embodiment, the housing 200 includes a tube 210 that is adapted to be pressed through the filter material from the fan side of the filter to provide a first opening 212 in the side of the filter receiving air to be filtered. In one embodiment, the tube 210 may be formed as a small sharp port that is used to puncture the filter media. A cap or locking nut 215 may fit over the tube and snap fit, friction fit, screw, or otherwise retain the housing in place to the filter while allowing communication of pressure via the first opening to one side of the differential pressure sensor within housing 200.

In some embodiments, the housing 200 with sensor or sensors may be reused on a new filter or filter media by removing the locking nut 215, removing the rest of the housing 200 from the filter and repeating installation on a new filter or filter media in the case of a filter frame allowing replacement of filter media. The housing with sensor or sensors may be installed on a filter frame and optionally reused.

A second opening, not shown, is positioned on the other side of housing 200 to provide communication of pressure from the fan side of the filter material to the differential pressure sensor such that the differential pressure sensor measures the pressure difference between the first and second openings.

The processing electronics (in this case built into the sensor ICs) converts the pressure measurements into an electrical input signal (in this case digital) for the Bluetooth communications electronics. In further embodiments, the processing electronics may be expanded to handle signals from other included sensors that provide air quality measurements (before and/or after the filter) in a facility or home, filter run time, humidity, etc.

The Bluetooth communication electronics transmits the sensor information to a user's Bluetooth device (i.e., smart phone, tablet, etc.) so that the user can monitor the filter's performance and know when to change the filter via one or more applications miming on the device. In addition to monitoring, the application(s) can be configured to notify the user when it's time to change the filter. The sensor may be powered by a coin cell battery. This coin cell battery will be easily replaceable by the customer. Other types of batteries, including fuel cells and rechargeable batteries may be used in further embodiments. The battery voltage level may be displayed and a battery low alert may be provided to a user to notify a user to change the battery.

Figure 3:
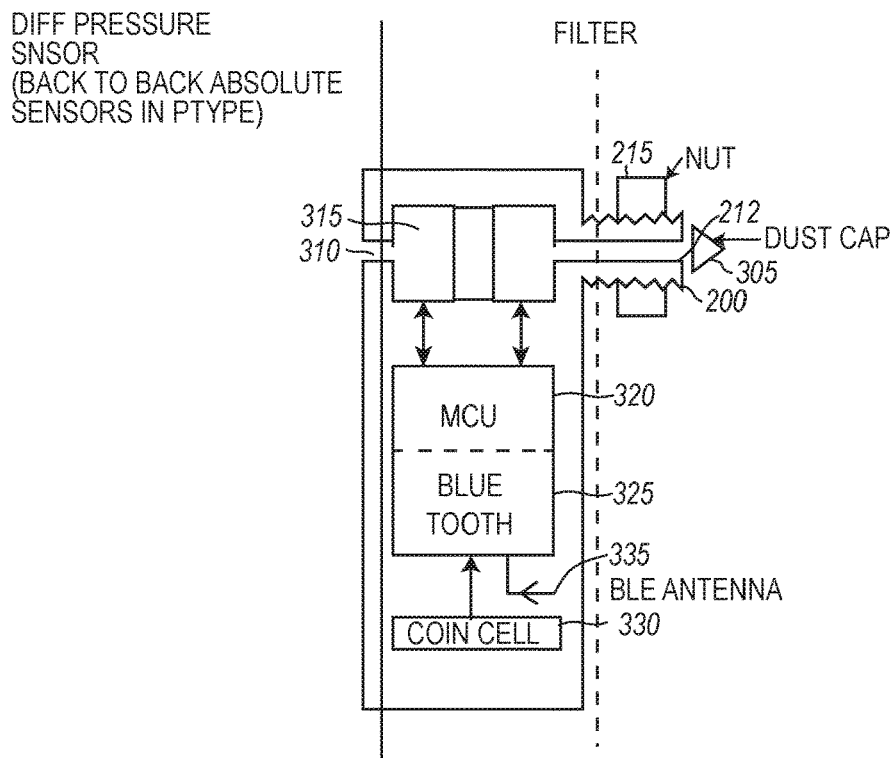
FIG. 3 is a block diagram of a filter with a differential pressure sensor according to an example embodiment.

A block diagram of an active air furnace filter sensor 300 is shown in FIG. 3. To prevent sensor clogging a small mechanical dust cap 305 may be molded onto the sensor nut 215. The dust cap 305 will prevent dust from clogging the sensor port. Sensor 300 may include a downstream opening 310, which in combination with an upstream opening 212 provides a pressure differential across a differential sensor 315, which in one embodiment may include back to back absolute pressure sensors, or a capacitive plate that flexes responsive to a difference in pressure across it, changing a capacitance of a circuit including the plate. A processor 320 may be programmed to receive sensed pressure data from the sensor 315 and perform analytics to determine the condition of the filter and generate alerts representative of such condition. A wireless circuitry 325, such as a Bluetooth communication circuit may be used by the processor 320 to communicate via a wireless network connection. A battery 330 may be used to power the processor, sensor, and circuitry. An antenna 335 is also coupled to the communication circuitry 325 for transmission and reception of wireless signals.

Figure 4:
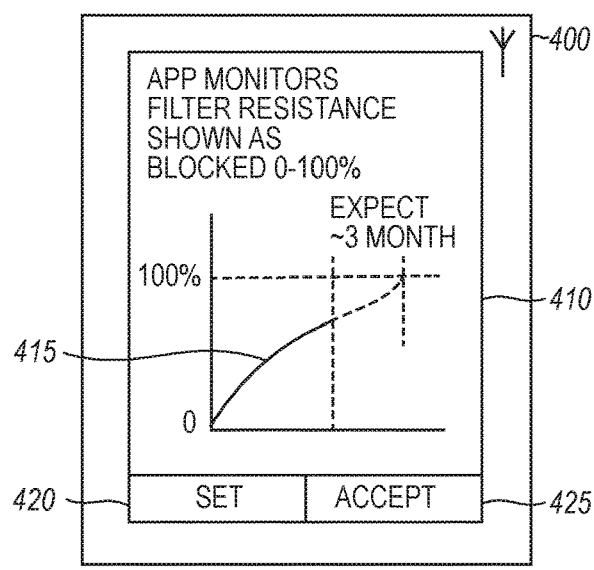
FIG. 4 is an illustration of a simulated user interface of an application running on a mobile device according to an example embodiment.

FIG. 4 is an illustration of a simulated, graphical user interface of an application running on a mobile device 400. The user interface in various embodiments provides an indication of the condition of a filter being monitored. The application receives communications from the sensor 300 representative of the condition of the filter and provides information to a user via the user interface indicated at 410. The user interface may include a graph 415 or other depiction illustrating filter performance, such as a line showing a percentage blockage of the filter, a percentage usage of the filter, and an expected time to replacement of the filter. The user may be provided with options, such as set 420 and accept 425. The options may include an option to automatically order a replacement filter at a time corresponding to a selected useful life remaining, or immediately upon determination that filter performance has deteriorated past a selected or determine threshold. The application may obtain replacement filter part information from the ID associated with the filter as described above via RFID or NFC reader, or even scanning a bar code or QR code on the filter. Alternatively, the ID associated with the filter may be communicated from the filter sensor to directly or indirectly to the device running the application via Bluetooth or other wireless communication protocol.

There are various methods which may be used to calibrate the filter sensor once it is installed in furnace system. Tests may be performed to determine the advantages and disadvantages of each calibration method.

Filter Sensor Calibration Method #1:
1. Install filter sensor in filter
2. Install filter into furnace system
3. Start device application
4. Push "Calibrate" button to set Differential Pressure=0
5. Start furnace
6. Press "Get Data" to take a Differential Pressure reading In some embodiments, the mobile device application may be used to scan a visible code or obtain information from the filter using RFID, NFC, or other wireless method to identify the filter. In some embodiments, the information necessary to identify the filter may be stored on the sensor and transmitted (directly or indirectly) to the mobile device. The identification of the filter may be used to check a table for proper settings to determine whether or not to notify a user that a filter should be replaced. If the filter identification is not proper, the app may be designed not to work with the filter. For example, the application may be configured to prevent a reset on a sensor that has already indicated the end of filter life. The application may store or access the sensor address and filter condition in memory and may prevent the user from pairing with a sensor that has been removed from a first filter and coupled to a second.

Filter Sensor Calibration Method #2:
1. Install filter sensor in filter
2. Install filter into furnace system
3. Start furnace
4. Start mobile device application
5. Push "Calibrate" button to set Differential Pressure=0
6. Press "Get Data" to take a Differential Pressure reading To check the performance and operation of the pressure sensing unit, two experiments were completed using the sensing unit on 1) lab scale hvac system and 2) an actual household furnace. The sensing unit was first placed in a lab scale HVAC system which has the ability to vary the blower speed, measure airflow rate, and measure pressure drop across the filter using a pressure transducer. With the ability to control the blower speed, this test was run using a wide range of airflow speeds to provide a range of sensor responses.

Figures 5A, 5B:
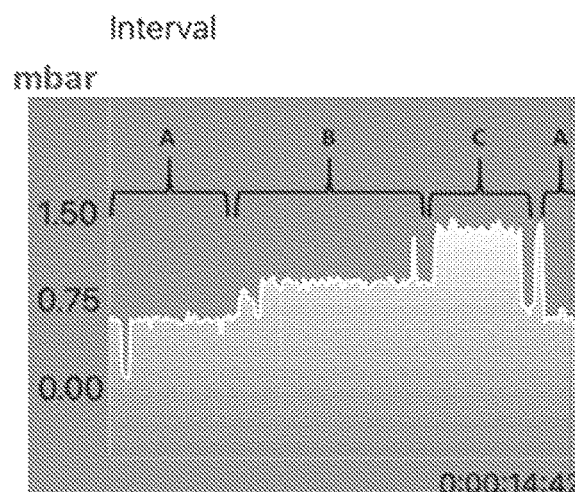
FIG. 5A is a table indicating blower speed in feet per minute, differential pressure sensor readings in millibars, duct pressure, a calculated pressure, and a letter, A, B, or C correlating results to a graph as shown in FIG. 5B according to an example embodiment.
FIG. 5B is a graph that illustrates the calculated pressure according to an example embodiment.

The sensor was mounted near the center of the filter and then installed into the filter holder and into the lab scale HVAC system. FIG. 5A is a table indicating blower speed in feet per minute, differential pressure sensor readings in millibars, duct pressure, a calculated pressure, and a letter, A, B, or C correlating results to a graph as shown in FIG. 5B that illustrates the calculated pressure. The blower speed was set to achieve a flowrate equal to 300 fpm (typical test velocity) through the filter. The test was allowed to run for several minutes to generate pressure drop data at steady state conditions. The blower speed was then increased to 400 fpm and 500 fpm to again measure the sensor responses at these higher airflow velocities. At each of the test velocities, pressure drop was recorded from the pressure transducer. The recorded pressure drop was then compared to the sensor pressure drop to establish a correlation on these responses.

Figures 6, 7:
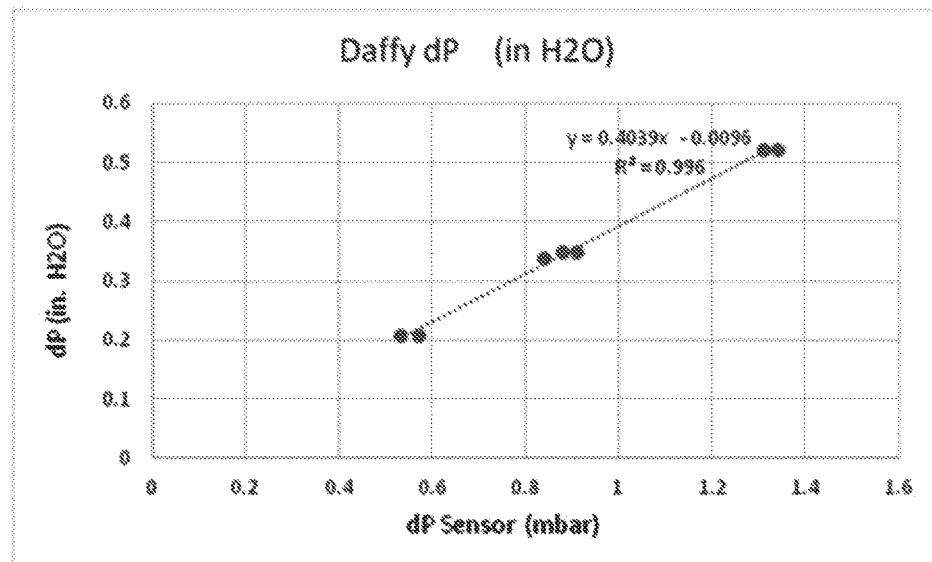
FIG. 6 is a graph comparing pressures obtained from a test with a blower running at different speeds according to an example embodiment.
FIG. 7 is a table similar to FIG. 5A according to an example embodiment.
Figure 8:
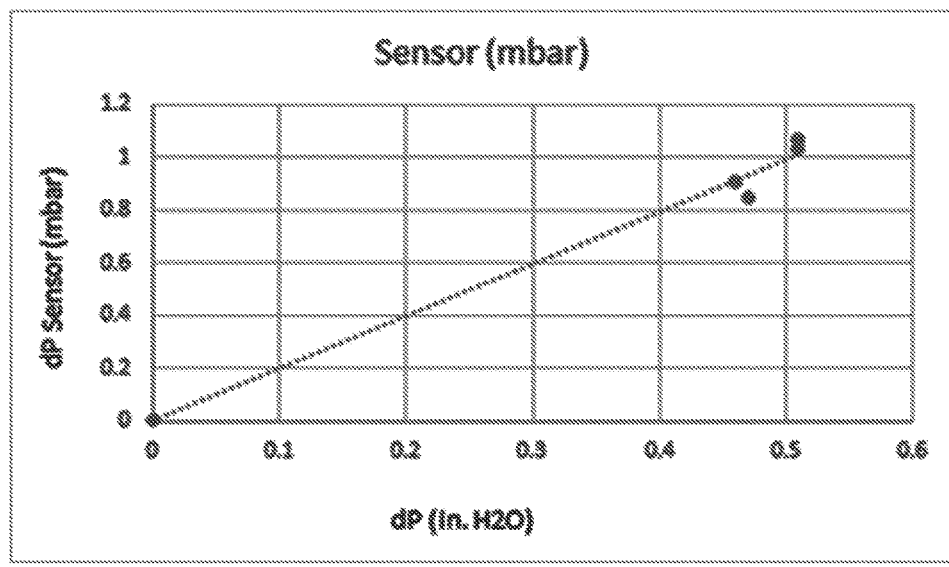
FIG. 8 is a graph comparing pressures obtained from a test with a blower running at different speeds according to an example embodiment.
Figure 9:
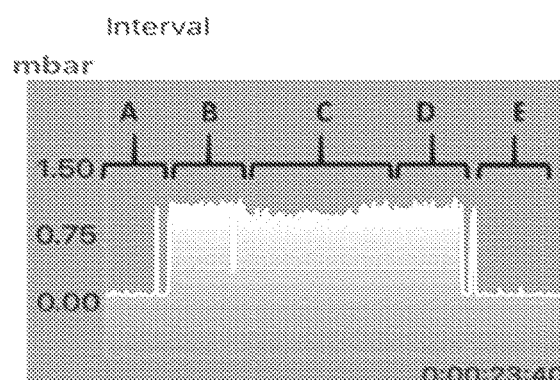
FIG. 9 is a graph showing pressures at different time intervals according to an example embodiment.

The results show a very good correlation between the lab scale HVAC system dP and the sensor dP ($R^2=0.996$, see FIG. 6 illustrating a plot comparing the pressures.) FIGS. 7, 8, and 9 illustrate a further test with HVAC modes changed, including a fan on and off with both AC on and AC off. Letters are again used to correlate the test results in the table in FIG. 7 with a graph in FIG. 9. FIG. 8 is a plot comparing the pressures in a manner similar to FIG. 6. A significant pressure difference is noted with the fan and/or AC on. In one embodiment, improved sensor sampling may result with the use of a filter with a thru-channel or designed channel that reduces or eliminates turbulence of air flow. In one embodiment, the sensors may be placed perpendicular air flow, shielded from direct air flow, recessed to air flow, set to some other angle than perpendicular that improves the sampling, set backward, or may have self-cleaning capabilities.

Figure 10:
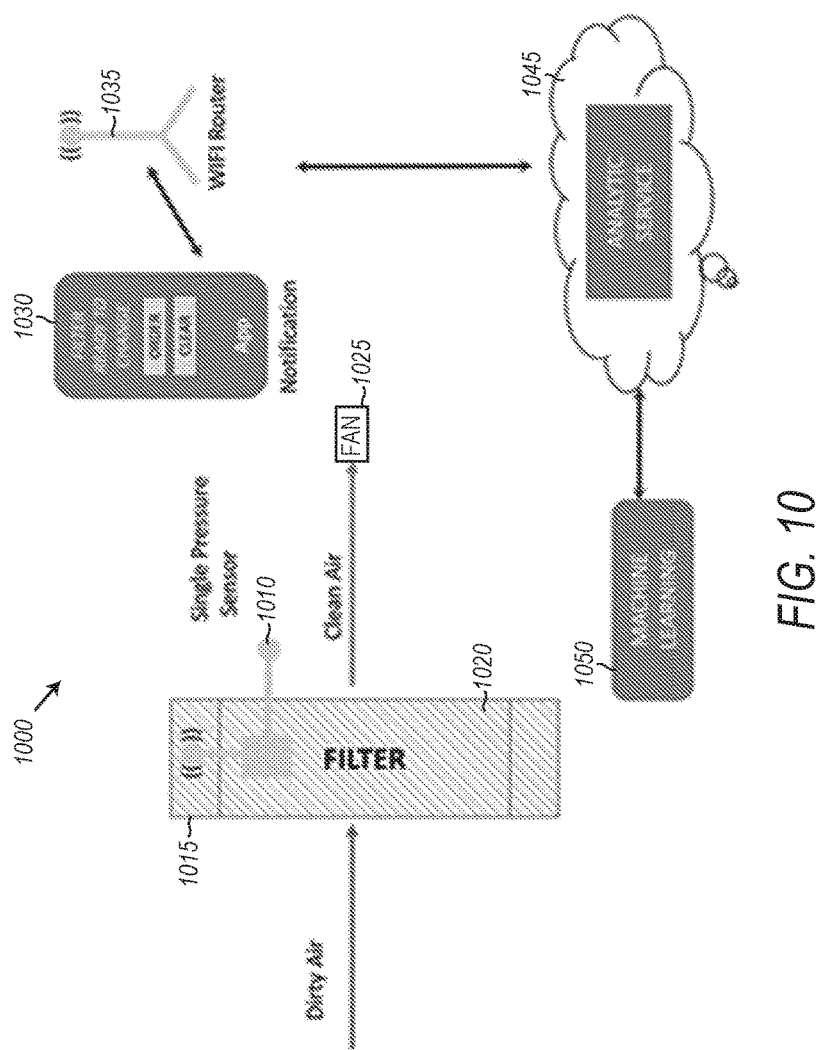
FIG. 10 is block diagram of a system for sensing obstruction of an air filter according to an example embodiment.

FIG. 10 is a block diagram of a device or system 1000 for sensing obstruction of an air filter according to an example embodiment. System 1000 includes a single pressure sensor 1010 on a clean side of a filter 1015. Sensor 1010 may be attached to the filter 1015 and provides pressure sensor or airflow capability on the clean side 1020 of the filter 1015 where the suction between the filter and a fan 1025 creates a pressure differential while the fan 1025, also corresponding to a furnace system, is running. The pressure and airflow between the filter 1015 and the fan 1025 decreases as the filter becomes obstructed with contaminants as the filter is aged by use.

The device may be powered by a coin cell battery. A larger battery pack could also be used for longer life. Preferably a power harvester will be used to generate power and recharge the battery using airflow, vibration, heat differential or other means. Data may be provided with a frequency of updates of many times a minute. More frequent updates or sensor samples may be provided in further embodiments, or may be reduced in rate to conserve battery life based on an expected life of the battery as compared to the expected time until the filter becomes significantly obstructed such that replacement is recommended.

In some embodiments, the sensor 1010 may include an accelerometer. The accelerometer sensor reading may be in the form of units of movement. The pressure sensor is in Pascal Units or Inches of Water (delta P at 85 lpm of airflow). An airflow sensor (vane, thermoelectric, bending, vibration) can also act as a substitute for the accelerometer and/or the pressure sensor in combination to determine characteristics in airflow and pressure on at least one of the clean side and the dirty side of the filter.

The communication can be to a mobile device 1030 or to a Wi-Fi router 1035 or other radio device to uplink to a cloud platform. Radio capability might include but is not limited to: ZigBee, Zwave, LoRa, Halo(new Wi-Fi), Bluetooth and Bluetooth BLE.

Data can be communicated directly to the application on the mobile device and/or directly to a cloud platform system 1045 via cellular connection, a Wi-Fi router or a hub. The sensors do not need to be calibrated before establishing a communication link. They can be calibrated during or after the initial activation of the device.

The device will self-calibrate using intelligent state management. The device may use an accelerometer or other sensor to identify when the furnace fan motor is off (reduced vibration or airflow) and when the fan motor is on (increased vibration or airflow). The off state will be used to calibrate and compare the device to the on state over time such as via a machine learning algorithm 1050.

Figure 11:
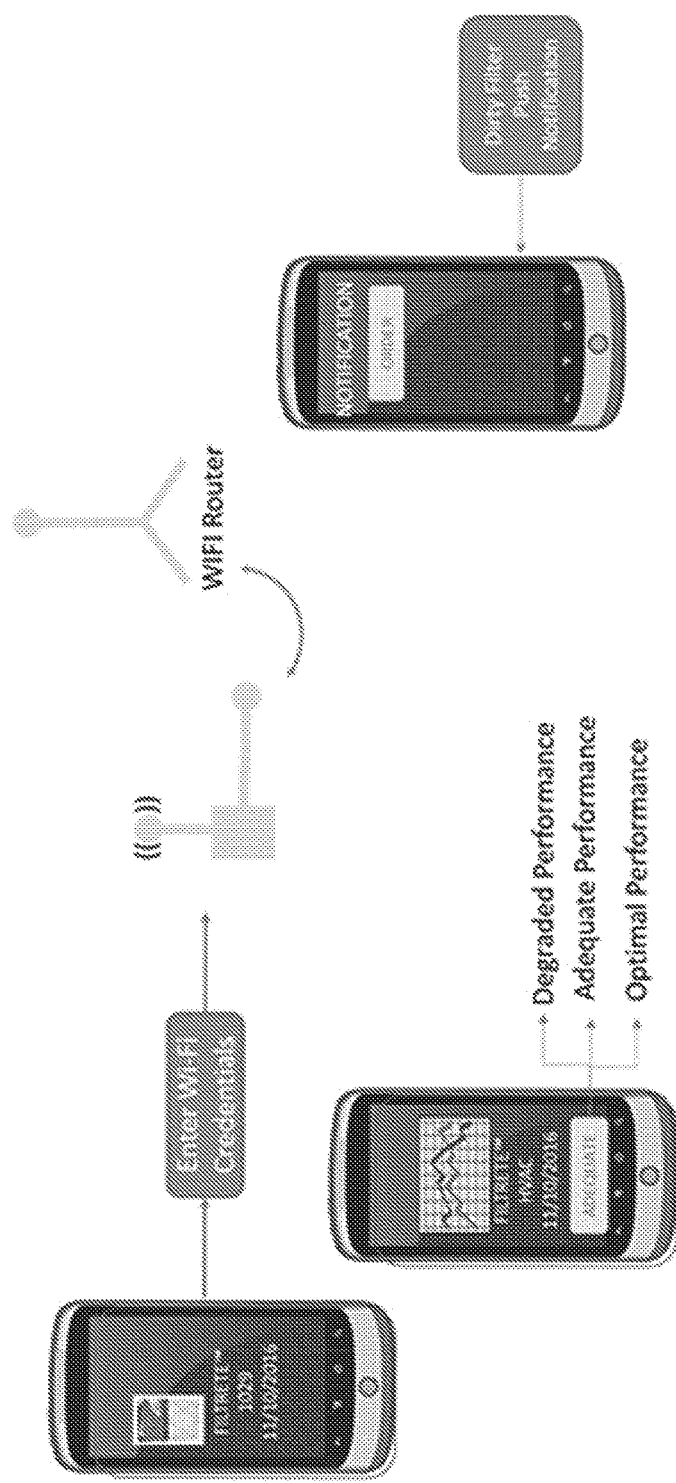
FIG. 11 is a block flow diagram illustrating configuration and use of a mobile device to interact with a filter sensor according to an example embodiment.

FIG. 11 is a block flow diagram illustrating configuration and use of a mobile device to interact with the filter sensor. Pairing with the filter sensor may occur, allowing entry of Wi-Fi credentials via the mobile device. This may allow the filter sensor to communicate directly with a router within a home of a customer/user. Updates of data from the filter result in presentation of a user interface to the user that indicates at least one of performance (e.g., degraded performance, adequate performance or optimal performance) and remaining useful filter life. A notification may also be sent that a filter may be dirty, obstructed, or otherwise in need of replacement, which may be displayed on the mobile device for the user to view, or may be programmed to automatically order a replacement filter or allow the user to select an option to conveniently order a replacement filter.

In some embodiments, specific user needs may be taken into account in the analytics that determine the need for filter replacement. A user may enter a profile indicative of specific medical conditions, such as pollen allergies or other respiratory conditions where higher than normal air quality may be desired. Such information may be used by the application to recommend a different filter, or to change thresholds for generating an indication of a filter in need of replacement. The ability to adapt to needs of the user may provide the user with a better overall experience and ease of use of the smart filter system, relieving them of having to more closely track the condition of a filter or save them from using a filter that is not capable of providing a suitable air quality needed for a better quality of life.

Figure 12:
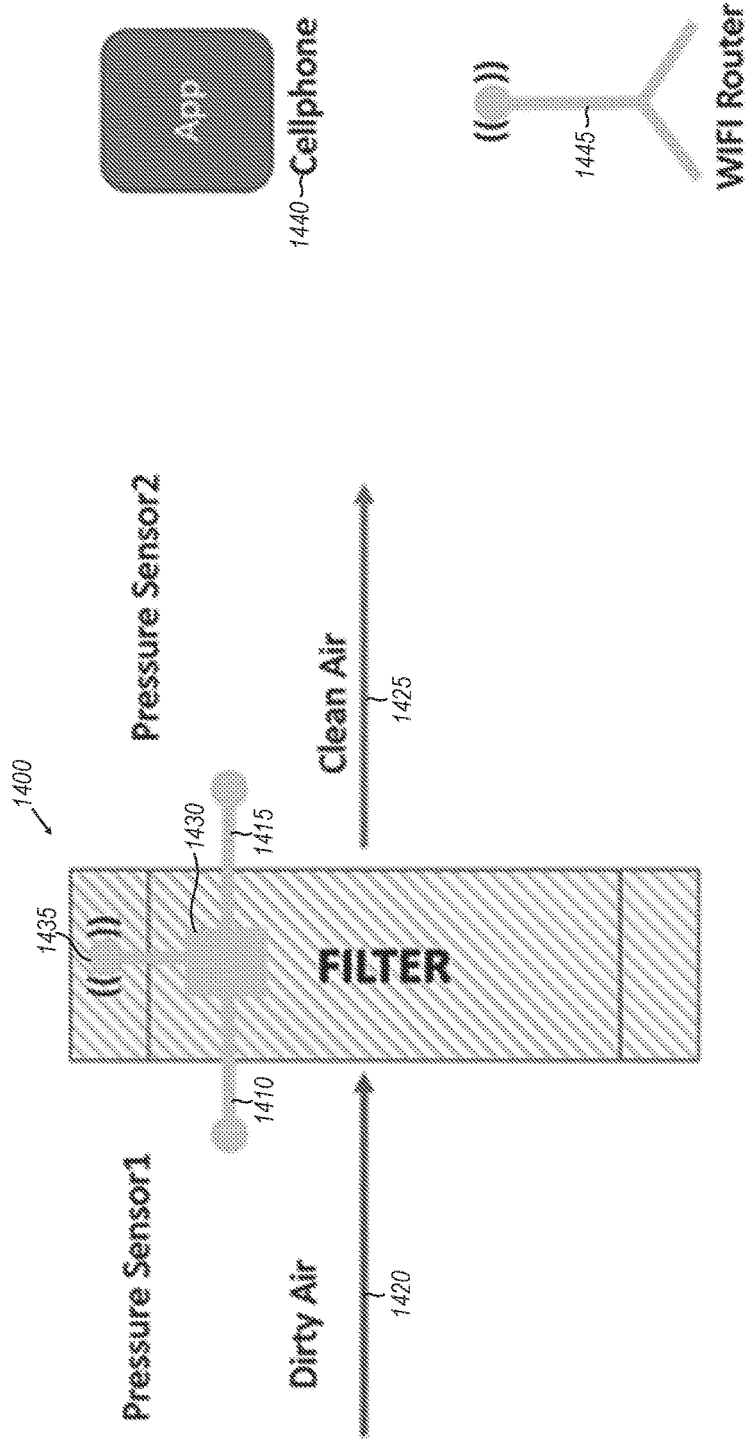
FIG. 12 is a block diagram of an example system utilizing two pressure sensors according to an example embodiment.

FIG. 12 is a block diagram of an example system 1400 utilizing two pressure sensors 1410 and 1415, one on each side of the filter. The use of two pressure sensors provides two independent pressure sensors to detect the air pressure before the filter (dirty side as indicated by dirty air arrow 1420) and after the filter (clean side as indicated by clean air arrow 1425). In one embodiment, the system includes two pressure sensors 1410, 1415, a circuit and/or logic 1430 that determines pressure difference as well as a radio (represented by antenna 1435) to communicate to cellphone 1440 via Bluetooth BLE, Bluetooth or Wi-Fi, indicated at router 1445.

A coin cell type battery may be used to provide power to system 1400. A larger battery pack or other type of power source could also be used for longer life. Data in the form of updates may be provided periodically, such as for example, once a minute. More frequent or less frequent updates or sensor samples could be provided as desired. Less frequent updates may help conserve battery life consistent with the length of time the filter is expected to function within desired parameters. The sensor reading in one embodiment is in Pascal Units or Inches of Water (delta P at 85 lpm of airflow). The communication can be to a cellphone or to a Wi-Fi router or other radio device to uplink to a cloud platform. Data may be communicated to the application directly on the phone and/or to a cloud platform system via the Wi-Fi router 1445. The pressure sensors do not need to be calibrated prior to use. In one embodiment, the pressure sensors may be calibrated during initial activation of the system.

Figure 13:
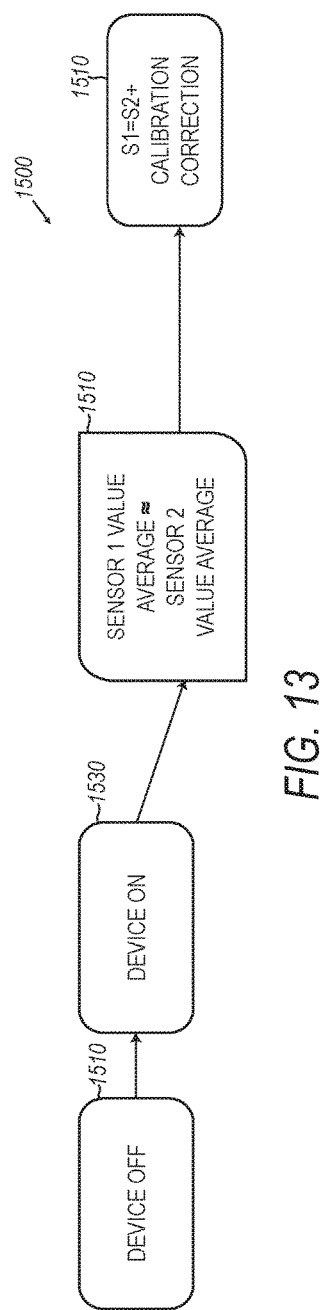
FIG. 13 is a block flow diagram illustrating calibration of pressure sensors according to an example embodiment.

In one embodiment, the two pressure sensors may be calibrated in the factory or in the initial setup relative to each other as indicated in a block flow diagram 1500 in FIG. 13. The calibration correction on the device will be represented by the equation S1=S2+Calibration Correction at 1510 when the airflow is zero. Calibration may be performed by reading pressures with the fan off at 1520 and the fan on at 1530. At 1540, the average values of the reading are determined for sensor 1 and sensor 2, and provided for calibration correction at 1510.

Example pressure sensors include: an AdaFruit BME280 I2c or SPI Temperature Humidity Pressure Sensor, an MPL3115A2-I2C Barometric Pressure/Altitude/Temperature Sensor (each available from Adafruit Industries, LLC) and the MPXM2010DT1 and MPXM2010D (available from NXP USA, Inc.). An exemplary, commercially available accelerometer is a LIS2DH12TR digital accelerometer from STMicroelectronics, Geneva, Switzerland. Any one of or both sensors may be off-the-shelf components that are readily commercially available.

Figure 14:
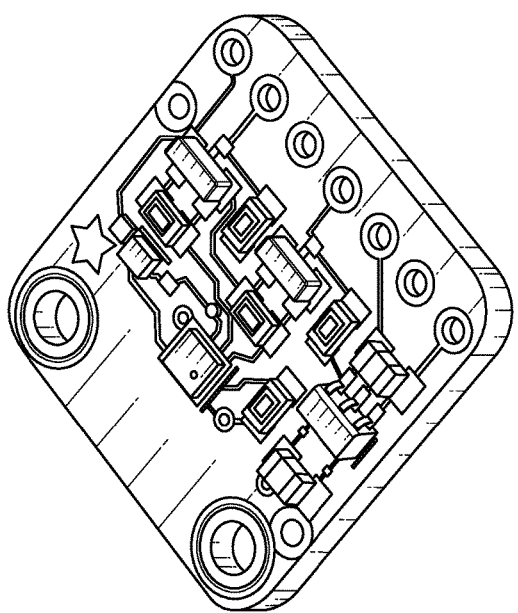
FIG. 14 provides information regarding an exemplary temperature and humidity sensor according to an example embodiment.

In a further example system, one or more sensors monitor pressure, air flow, air quality, temperature, humidity, distortion of the filter, airflow characterization and vibration on the clean and dirty side of the filter (before and after the filter). An example humidity sensor, an AdaFruit BME280 I2c or SPI Temperature Humidity Pressure Sensor, is shown in FIG. 14.

Figure 15:
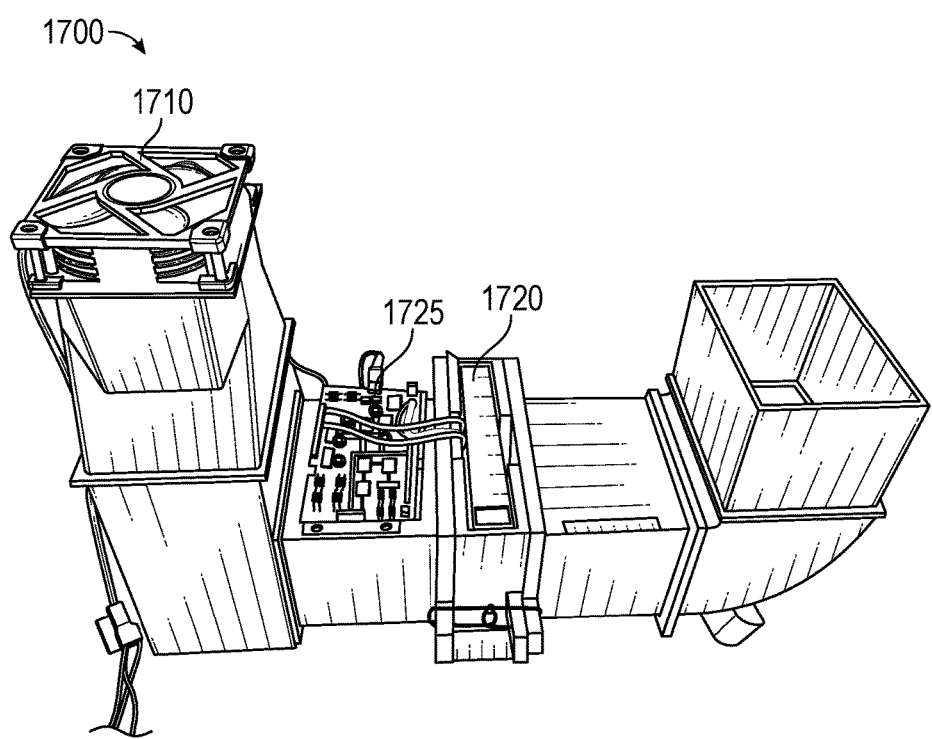
FIG. 15 is a photograph of an experimental system for testing a smart filter according to an example embodiment.

A lab scale furnace experimental system 1700 is indicated in FIG. 15. A fan 1710 having a controllable fan speed draws air through simulated ductwork that has a filter 1720 in the center of the duct work and sensor circuitry 1725 in the form of a circuit board. The sensor circuitry 1725 receives data from one or more sensors measuring one or more parameters representative of filter condition and transmits the resulting information as described above. The sensor circuitry 1725 may implement an internet of things (IoT) application protocol to automatically upload and maintain data on a remote platform for real-time viewing, retrieval, and analysis.

Figure 16:
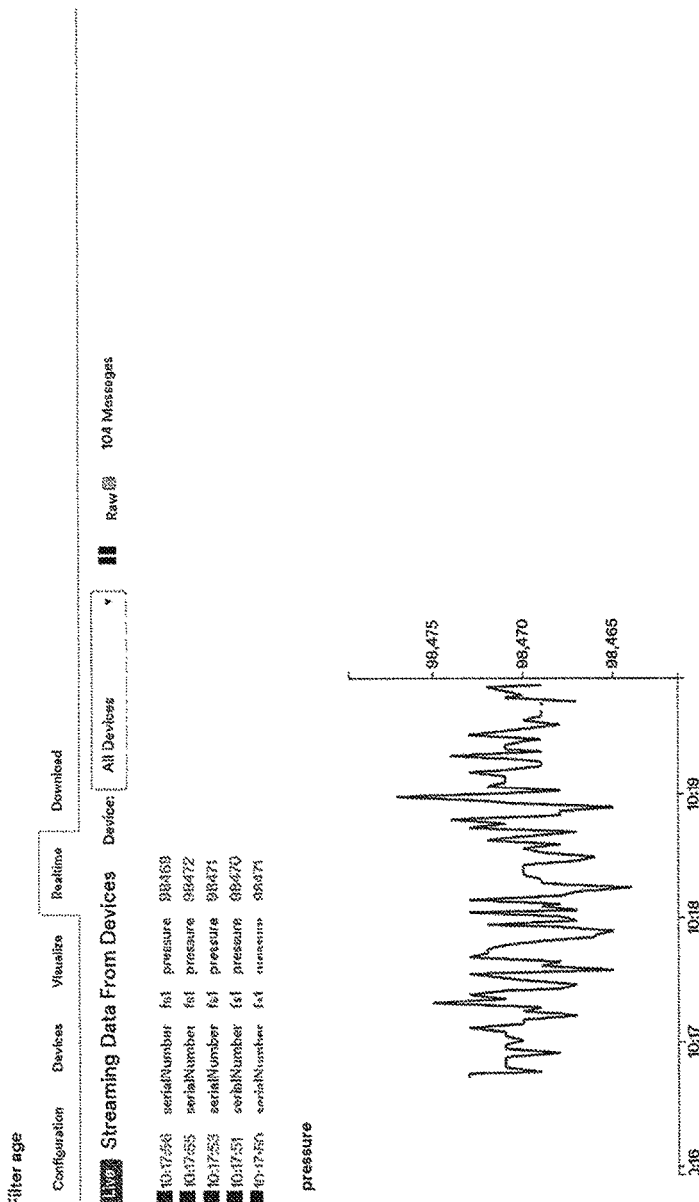
FIG. 16 provides representations of data streaming from smart filter circuitry according to an example embodiment.

FIG. 16 shows an example of data streaming from the circuitry 1725, which may be wirelessly coupled to a network via an internet of things (IoT) protocol.

Figure 17:
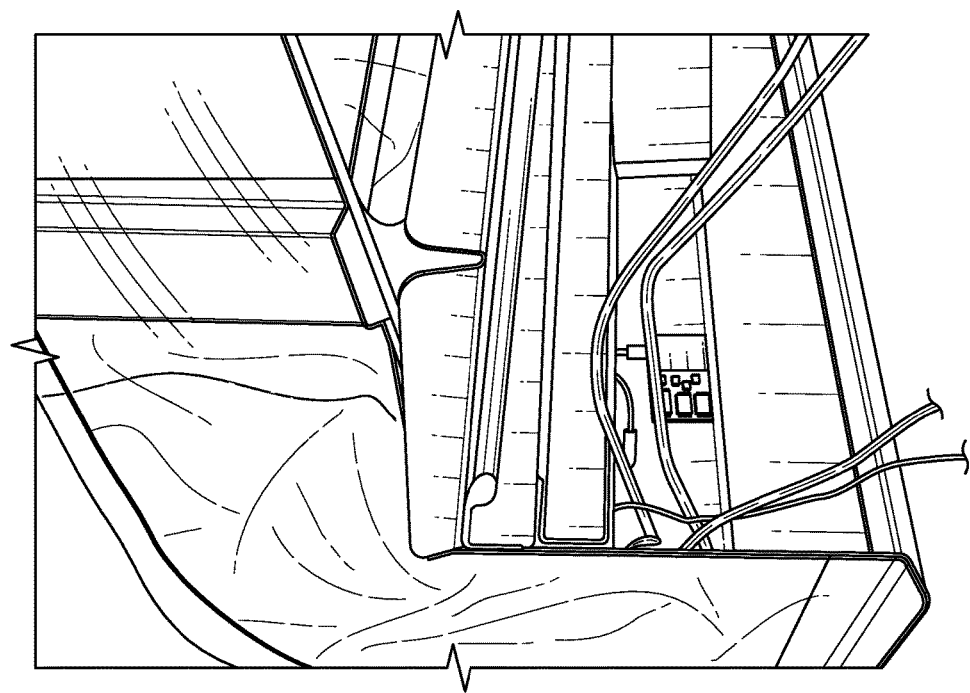
FIG. 17 is photograph of a filter installed in common home consumer furnace ductwork according to an example embodiment.

FIG. 17 is a picture of a filter installed in common home consumer furnace ductwork that provides a larger test environment. Sensor packs may be installed before and after the filter. One sensor pack is visible in the space between the filter and motor for testing. There is a second sensor pack on the left before the filter (for testing/calibration). A Wi-Fi signal is able to penetrate the metal furnace without issue in this configuration with the plugged-in sensor pack. The sensor pack may for example be a Raspberry Pi3 with a "sensor hat" that is connected to power to provide a very rapid sampling rate for high resolution test data. The data is being uploaded to an IoT Platform. Initial tests indicated that the sensors are able to pick up the pressure difference before the filter and after the filter. The sensors may be run over several days as a "clean" filter to determine the variance and sensitivity of the sensor over a longer period of time.

Figure 18:
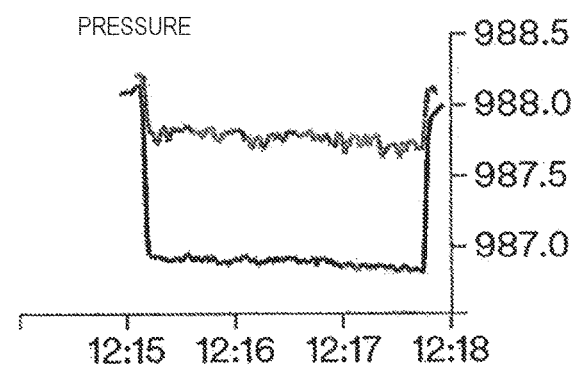
FIG. 18 is a graph illustrating the difference in pressure across a filter with the fan first off, then on, then off again according to an example embodiment.

FIG. 18 is a graph illustrating the difference in pressure across a filter with the fan first off, then on, then off again. When the fan is off, the difference in pressure is negligible if not zero. The top line represents data from the sensor upstream of the filter and the lower line represents data from the sensor downstream of the filter. Note that when the furnace is off at the beginning of the graph and also at the end of the graph, the two lines rejoin.

Figures 19, 20:
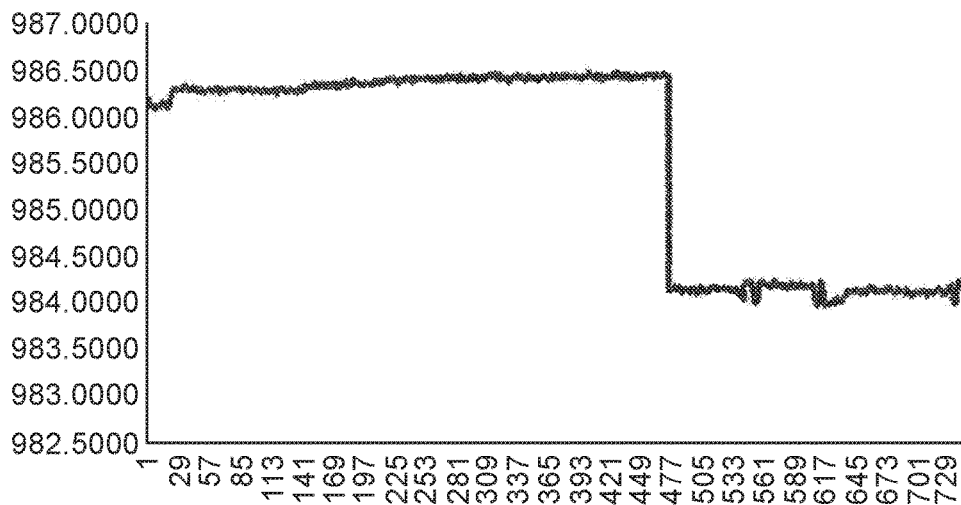
FIG. 19 is a table indicating information transmitted and collected during operation of a system including a smart filter according to an example embodiment.
FIG. 20 is a graph indicating readings from a single downstream side pressure sensor with the furnace or fan off, and then on, where the filter is known to be dirty and in need of replacement according to an example embodiment.

FIG. 19 is a spreadsheet based table indicating information transmitted and collected during operation of a system including a smart filter.

"States" of operation are identified for the furnace at the point of the individual sensor unit being initiated with a filter change. These states include:

Furnace Off—The furnace assumes the pressure level of the ambient air while having a low level of vibration.

Furnace On Clean Filter—The clean side sensor establishes a level of pressure.

Furnace On Variation 1 . . . n—The furnace establishes several potential regular "states" as it runs over time. These states are established during the 2-month phase of the filter in use.

Furnace On Dirtying—Levels of obstruction are determined relative to the Furnace On Variation states established during the first two months.

Furnace Filter Needing Changing—Is established when the furnace filter reaches a predetermined state, such as for example, an average of 1.5 pascals of pressure less than that of a previously established state or 3.25 months has been reached during Furnace On relative to any state.

The data file from a first Experiment 1 on the full-sized furnace was reviewed with the following averaged results as follows.

Before Filter—Pi Serial Number 43—off calibration Average 986.3636

After Filter—Pi Serial Number 36—off calibration Average 986.3614

Before Filter—Pi Serial Number 43—clean running Average 986.2444

After Filter—Pi Serial Number 36—clean running Average 985.8823

Before Filter—Pi Serial Number 43—unknown dirty Average 986.0958

After Filter—Pi Serial Number 36—unknown dirty Average 985.2246

Before Filter—Pi Serial Number 43—dirty 0.74 Average 986.1727

After Filter—Pi Serial Number 36—dirty 0.74 Average 985.2684

Before Filter—Pi Serial Number 43—dirty 1.54 Average 986.3910

After Filter—Pi Serial Number 36—dirty 1.54 Average 984.1002

Initial results demonstrate the ability of low cost sensors being able to establish the pressure differential between the before filter and after filter sections of the furnace. The results also suggest the ability of a system to establish states over time with one or more sensors effectively. The "furnace off" state would allow for one or more sensors to calibrate relative to atmospheric pressure changes as well as furnace configuration changes over time.

Algorithm Method

A system including one or more pressure sensors in addition to accelerometer sensors can establish states of the furnace over time:

S0—Filter Installation—Furnace Off
S1—Filter Clean—Furnace On
S2 . . . n—Self Characterized States within Month 1-2
Sr—In Need of Replacement—Characterized by an average change of 2+ pascals difference from S0 or from pre-filter pressure sensor while in the on state relative to S0 or 1.5+ pascals as compared to any of S2 . . . n Self Characterized States.

Since different type of sensors that sense different parameters that may be directly representative of filter media condition may be used in different embodiments, a more generic algorithm may include similar steps that are not limited to the use of only pressure sensors. The "in need of replacement" thresholds may be based on a change in airflow, a change in motor loading, changes in vibrations, and other parameters sensed by appropriate sensors as described in further detail below.

Additional Methodology Detail

State Value—The value of a state is calculated via a multistep process. The primary deterministic state is the condition of the furnace being on or off. The second step is a stabilization period, such as a delay of two minutes after the furnace turning on or off for airflow, vibration and pressure stabilization. The third step is to gather data for a period of time (e.g., two minutes). Outlier data of 2× the moving average is removed and the moving average for the period is established for the after filter pressure sensor. Vibration (accelerometer data) can be used to further determine the on/off state of the furnace. Initial experimentation suggests that a single sensor can be used for this determination.

Additional Contributing Factors

Room air pollution information (particulates and other contaminates) can be used to improve the accuracy of the need to change air filtration media.

Metadata/General Survey Information—Smoking, use of candles, ownership of pet information can be used to inform the algorithm to more aggressively determine change.

General Building Configuration—Windows open/closed, carpeting as well as other information can be used to inform the algorithm.

Outdoor Air Pollution—Information can be gathered from air quality monitoring sites to determine aggressiveness of replacement.

Analytics may be used to filter and provide air quality advice, furnace status and filter replacement status throughout the life of the filter. The system may be powered by a coin cell battery. A larger battery pack could also be used for longer life. A power harvester may be used to generate power and recharge the battery using airflow, vibration, heat differential or other means. Other power sources and storage methods can be used as needed. The system may provide updates at various time intervals, such as many times a minute. More frequent updates or sensor samples could be provided. Frequency of updates may be controlled by air movement.

Air pressure may be measured before and after the filter to be able to determine pressure difference. Multiple sensors may be used to correct for failure of individual sensors. Filaments and airflow sensors may be included to provide a map of air turbulence within the air chambers before and after the filter. The air turbulence information can be used to determine obstruction or sub optimized performance of the filter or furnace controls.

Air quality may also be monitored before filter and after filter to provide particulate and non-atmospheric gas values to monitor filter performance and air quality before and after treatment. Air quality monitors/sensors may also be disposed outside the HVAC system and within the building or home. Air temperature in the air stream may also be monitored. Air humidity in the air stream may also be monitored. Strain sensors may be used to monitor the distortion of the physical filter shape during the life of the filter. Strain gauge capability may be woven into the filaments of the filter.

Directional (gyroscopic) and non-directional (accelerometer) measurements may be provided by sensors to understand vibration which may result in relative strain within the components of the furnace system. Communication capabilities may be included to provide information to a mobile device such as a cellphone or to a Wi-Fi router or other radio device to uplink to a cloud platform. Radio capability might include but is not limited to: ZigBee, Zwave, LoRa, Halo (new Wi-Fi), Bluetooth and Bluetooth BLE. Data, including notifications, can be communicated to an application directly on the mobile device and/or to a cloud platform system via the Wi-Fi router. Note that the sensors do not need to be calibrated beforehand. They can be calibrated in the initial activation of the device.

FIG. 20 is a graph indicating readings from a single downstream side pressure sensor with the furnace or fan off, and then on, where the filter is known to be dirty and in need of replacement. Note that the pressure changes by more than 2 pascals, moving from almost 986.5 pascals when off to less than 984.5 pascals when on. By recording pressure both when the fan is on and off, the difference may be found by subtraction. Comparison to a threshold of 2 pascals indicates that the threshold has been exceeded based on the data shown in FIG. 20.

The pressure in uncalibrated pascals (low cost sensor) is on the left (Y-axis) (982-987) over time with the time increments on the X axis. The sample experiment data shows the off state changing from a high pressure of 986.5000 to approximately 984.0000 when the furnace is turned on. The pressure differential is produced by the difference in ambient air pressure (approximately 986) is obstructed by the fan operation of the furnace fan behind the obstructed fan which produces an air pressure reduction to approximately. 984.

A single pressure sensor can be used to determine furnace state (on or off) by the rapid nature of the pressure change. Atmospheric pressure change occurs more slowly. The on/off periods can be used to determine the comparator for the determination of the state Sr (need to change the filter).

Figure 21:
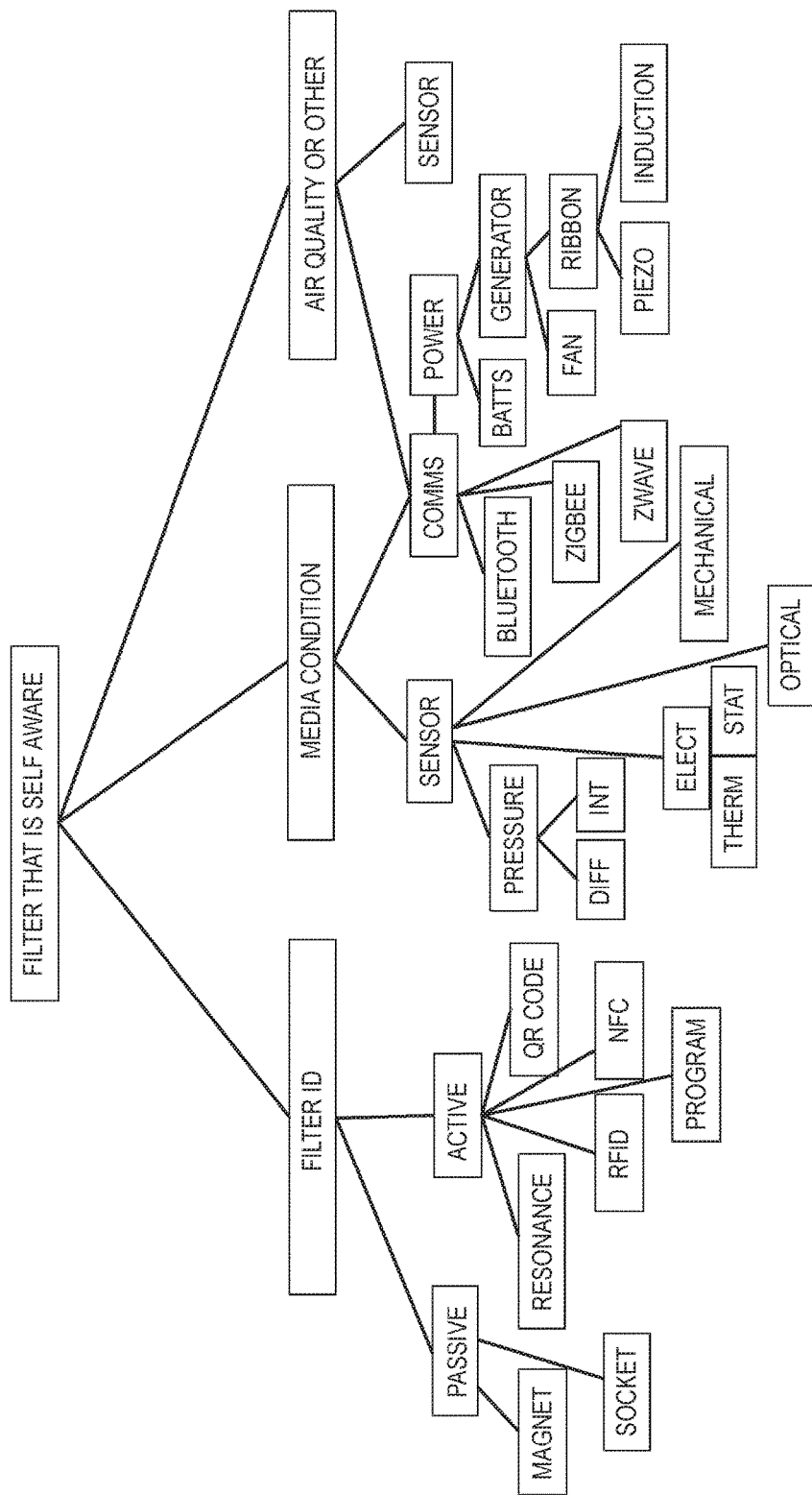
FIG. 21 is a block diagram representation of a smart filter with various options for providing an ID of the filter, sensing the filter media condition, and optionally sensing air quality according to an example embodiment.

Several different example embodiments have been described above. FIG. 21 is a block diagram representation of a smart filter with various options for providing an ID of the filter, sensing the filter media condition, and optionally sensing air quality. Further details regarding the options is provided with a discussion of FIG. 22.

Figure 22:
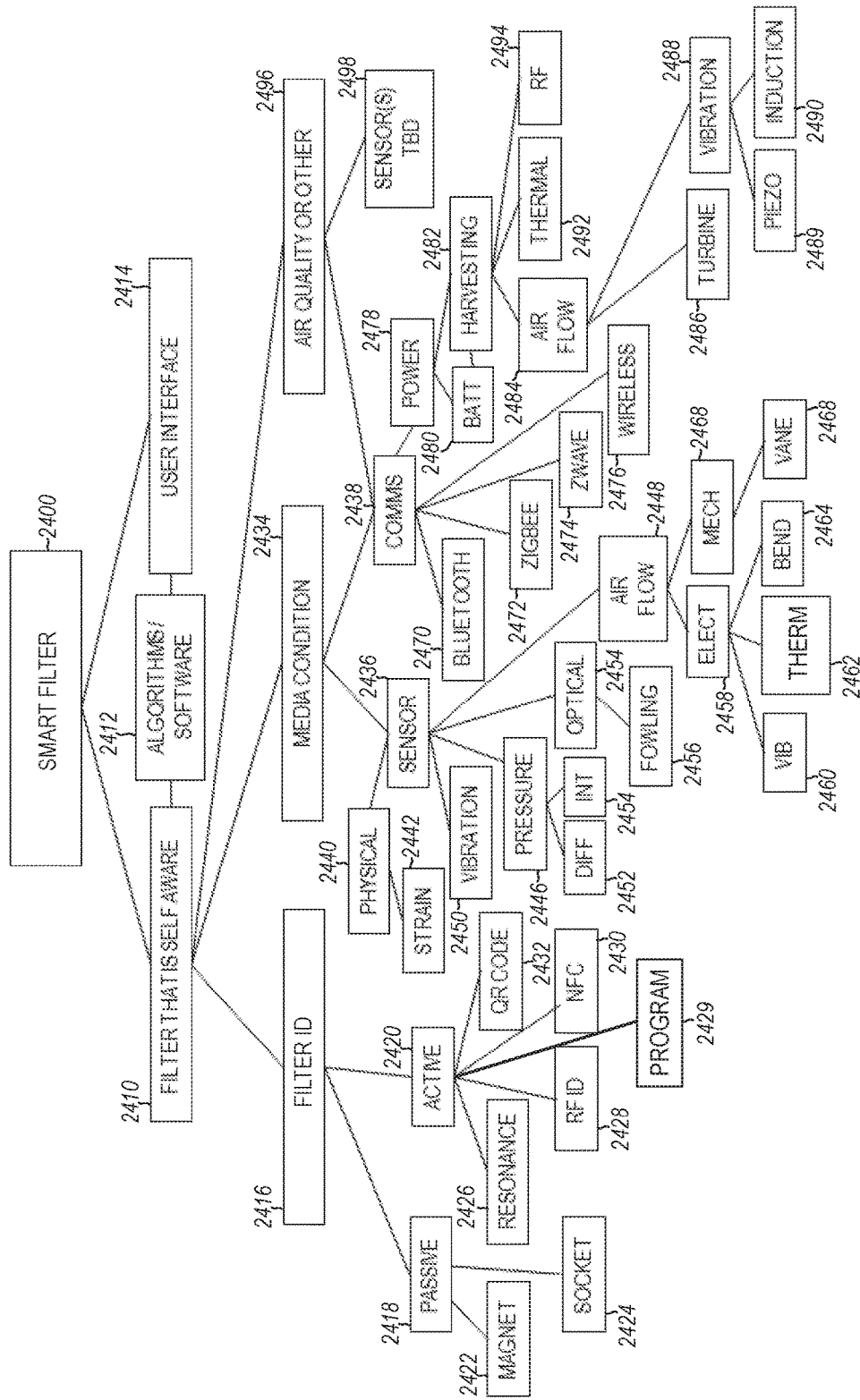
FIG. 22 is a block diagram representation of multiple elements and alternative elements in a smart filter system according to an example embodiment.

An overall smart filter system view with various options is now described. FIG. 22 is a block diagram representation of multiple elements and alternative elements in a smart filter system 2400. System 2400 comprises three major elements, an air filter 2410 that is self-aware when in use, software algorithms 2412 that collect data from the filter 2410, and a user interface 2414 to display relevant information on a display, such as a mobile device display. The mobile device may be a laptop computer, cellular telephone, tablet, or other device capable of receiving, processing, and displaying information.

Self-Aware Filter 2410 may be self-aware by means of a circuit incorporated into the filter, attached to the filter during installation, or in a frame the holds the filter. Once the filter is installed, it can identify that it is a particular brand, type, or size of filter, and provide digital data about the filter during operation. In addition, the filter may provide data regarding air quality of air moving through the system 2400.

Software algorithms 2412 collect data from one or more sensors and manipulate the data for future analysis, and store multiple data strings (from multiple collection sessions) for future transmission and reporting.

The user interface 2414 presents the data in a format that lets the end user readily see filter performance. It may provide historical data and/or current conditions. It may offer a prediction of time to filter replacement based on filter condition and time of use. It can provide data in any format useful to the consumer including alerts and automatic ordering capabilities. It may display air quality data at a room, building, facility, or campus level. Air quality data may be pulled from external air quality monitoring services, air quality monitoring devices outside the HVAC system, or one or more sensors in the HVAC system.

A Filter ID 2416 can be passive 2418 or active 2420. Passive ID embodiments may include use of a magnetic switch 2422 which closes when the filter is inserted, or by having a simple socket 2424 built into the filter that activates the circuit when it is plugged in. Active means 2420 could be accomplished by means of a passive resonant circuit 2426 attached to an HVAC device which resonates when the filter and sensor circuit are installed therein. Other means could be used to detect the filter such as RF ID tags 2428, NFC tags 2430, or by reading a bar code or QR code 2432. In another embodiment, the Filter ID may be programmed on the sensor 2431 and communicated from the sensor via Bluetooth or other wireless communication protocol to a mobile device or cloud platform.

Media Condition 2434 can be determined by an electronic data collection circuit and a sensor 2436, and reported by wireless transmission shown under a communications block 2438. There are a variety of sensors 2436 that may be used in order to evaluate the condition of the filter. A physical sensor 2440 can evaluate eventual bowing of the filter using a strain gauge 2442. Other sensors that could be used include optical 2444, pressure 2446, air flow 2448 or vibration 2450. There are a number of different versions of each type of these sensors. The pressure sensor 2446 may be a differential pressure sensor 2452 or a single pressure sensor 2454 that may integrate pressure over time or compare pressure measurements when a fan is on and off.

Optical 2444 media condition sensing may detect fowling 2456 by measuring transmission of light through the media via a photodetector for example. Airflow 2448 may be indicative of fan operation, which may be used in conjunction with a pressure measurement from a single downstream filter to determine the condition of the filter. In further embodiments, airflow sensors may be used to measure the change in airflow over time, with decreased airflow being associated with a deteriorating condition of the filter media. A threshold corresponding to the decrease in airflow may be used to determine that the filter should be replaced. Airflow may be measured by electrical means 2458 including for example vibration sensor 2460, thermoelectric sensor 2462, or bend sensor 2464 (piezoelectric based in one embodiment). Mechanical means 2466 of sensing may include a vane based sensor 2468 to measure air turbulence, which may represent fan operation as well as filter media condition, as turbulence may change responsive to deterioration of filter media condition. Each of these sensors provide information regarding operation of the fan. In some embodiments, operation of the fan may be detected by measuring current flow to the fan to provide an indication of loading on the fan motor, which may be directly representative of the condition of the filter media.

When data from multiple sensors is collected, the data may be fused in multiple different ways to determine the filter media condition. For instance, data representative of fan operation may be used with a single downstream pressure reading in one embodiment. Vibration information may be combined with pressure in a further embodiment. Multiple vibration and turbulence measurements may be used in further embodiments. Many different sensors, either individually or combined may provide information from which the condition of the filter media may be calculated in various embodiments, either from the information of any one or of the sensors or from information fused from multiple sensors.

Data that is collected can be communicated at one or more options under communications 2438. Communications by wireless means can be accomplished using a variety of wireless protocols including wireless 2.4 GHz or 5 GHz, Bluetooth or Bluetooth BLE 2470, ZigBee 2472, Zwave 2474, Halo, or other standard or custom protocols represented at 2476.

Power 2478 for circuitry, including sensors, can come from a variety of sources. One option is a battery 2480. Alternately, energy for operating the circuit can be harvested 2482 from the environment. Examples could be devices that generate power from air movement 2484 when the HVAC system is in operation, such as a turbine 2486 or via vibrations 2488 utilizing an oscillating ribbon with piezoelectric 2489 or inductive generators 2490. Alternately power could be generated using the thermoelectric effect 2492, or power could be supplied externally with an RF transmission signal 2494.

Air Quality 2496 can be defined in a number of ways depending on many factors but could include measurement via sensors 2498 of particulate on the clean air side, measuring VOCs, measurement of particulate in a given room or building, etc.

Under certain circumstances, the smart filter system may lack information sufficient to determine media condition based solely on data from a sensor or multitude of sensors. For instance, the user may leave the home for a week and yet leave his or her HVAC system running. As another example, the user may move to a location in the home or facility beyond the reach of the wireless communication signal. Each circumstance results in potential loss of data communication between the sensor and the user's mobile device, but the filter condition will continue to deteriorate. Depending on the duration of the communication loss, the Media Condition reported to the user may not accurately reflect status of a filter media. In these and other situations, it may be possible to supplement an output of a predictive filter replacement algorithm for sensor data over the requisite time period.

In one example, the missing data is supplemented by estimating replacement status as a function of HVAC fan runtime. Fan runtime can be estimated using outdoor weather data and can be adjusted in accordance with parameters relevant to the particular air filter and/or HVAC system operating conditions, such as dwelling parameters, HVAC use parameters, user preference parameters, and filter parameters. The weather data can be obtained for a particular region, for example, from an online data service. The weather data can be used to estimate air filter runtime, and the air filter runtime can be used to estimate the replacement status of the air filter. Exemplary methods for estimating filter replacement status as a function of fan runtime are described in International Publication No. WO 2016/089688 (Fox et al.), which is incorporated by reference in its entirety herein.

Figure 23:
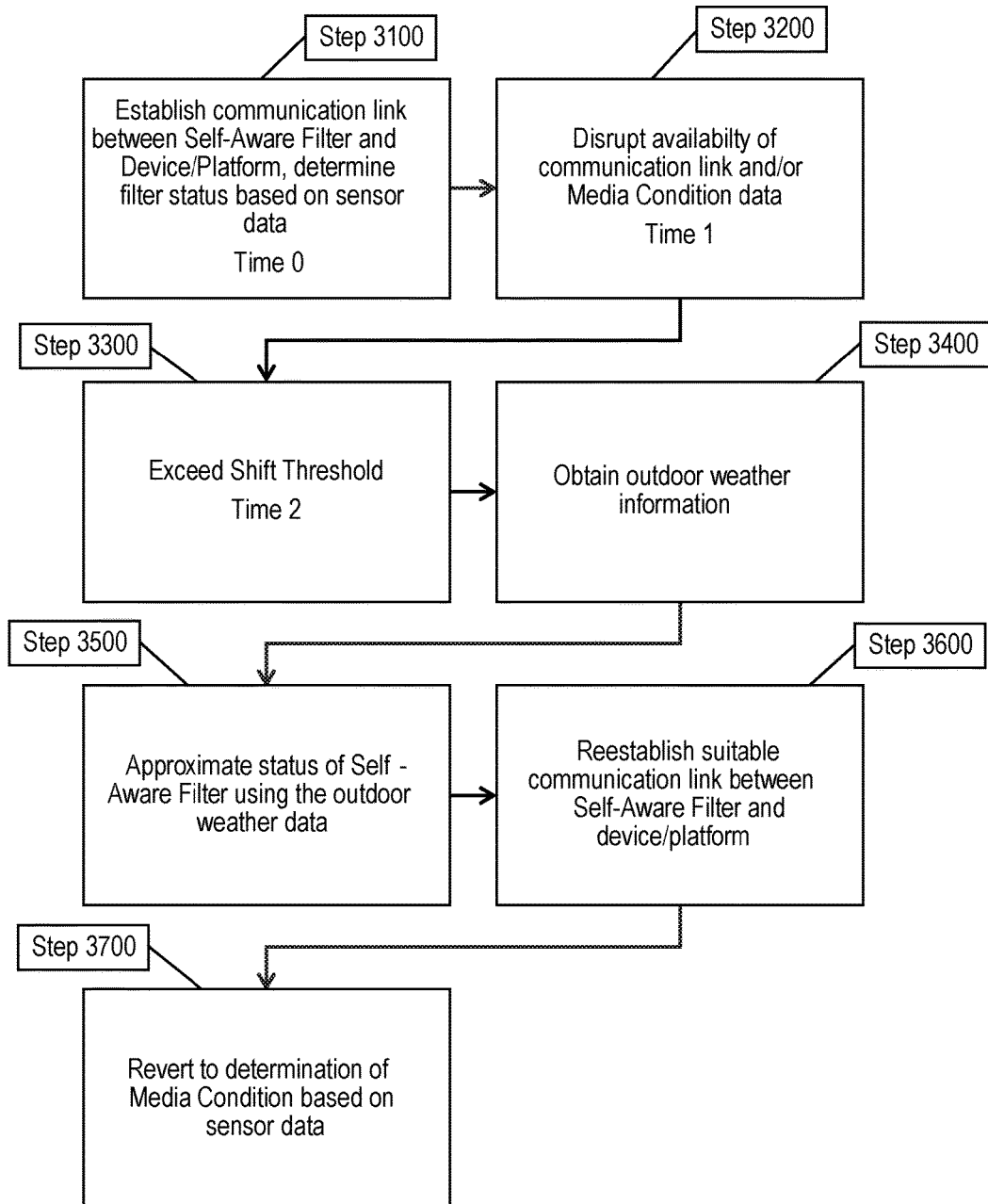
FIG. 23 is a block flow diagram illustrating the configuration and use of information from a plurality of sources to determine filter life according to an example embodiment.

FIG. 23 illustrates an exemplary sequence for shifting between sensor data and estimated status in reporting filter condition. At Step 3000 and "Time 0" a communication link is established between a Self-Aware Filter and a mobile device or cloud platform. At step 3100 and "Time 1", the communication provides substandard or no data from the sensor. Data may be substandard, for example, if a confidence value assigned to a given output parameter is not met or exceeded. In Step 3200 and "Time 2", the time period of substandard or lacking data reaches or exceeds a Shift Threshold, which may be based on, e.g., the amount of time between successful communication links or predictive results. Once the Shift Threshold is exceeded, outdoor weather data for a geographical region related to the HVAC system is obtained (e.g., electronically retrieved from an online data service) in Step 3300. Outdoor weather data can be collected contemporaneously with data from the sensor(s), or such collection may be triggered upon reaching the Shift Threshold. In Step 3400, the replacement status of the air filter is approximated using the outdoor weather data. For example, the outdoor weather data is used to estimate air filter runtime, and the air filter runtime is used to estimate the replacement status of the air filter. The estimation can be provided to the user via the user interface, which may or may not share a sensory experience similar to estimation premised primarily on sensor data. At Step 3500, the Self-Aware Filter establishes a communication link with the user's mobile device and/or relevant output parameters are deemed acceptable at "Time 3". The system may immediately (or near-immediately) shift back to predicting filter condition based on data received from the sensor, or may continue operating based on weather-based estimation until a suitable link is established for a time period exceeding a Reversion Threshold at Step 3700.

An experiment using two sensors, one before a filter and one after the filter produced the following results during different states (conditions). Using the pressure difference between the $P_1$ and $P_2$ sensors (before filter and after filter respectively) as a determination for filter obstruction measurement is well understood. Determining if a single sensor before the filter or a single sensor after the filter can provide enough information to determine filter obstruction was not previously understood.

A sample of data during different states of operation for an experimental furnace provides the following graph data.

Figure 24:
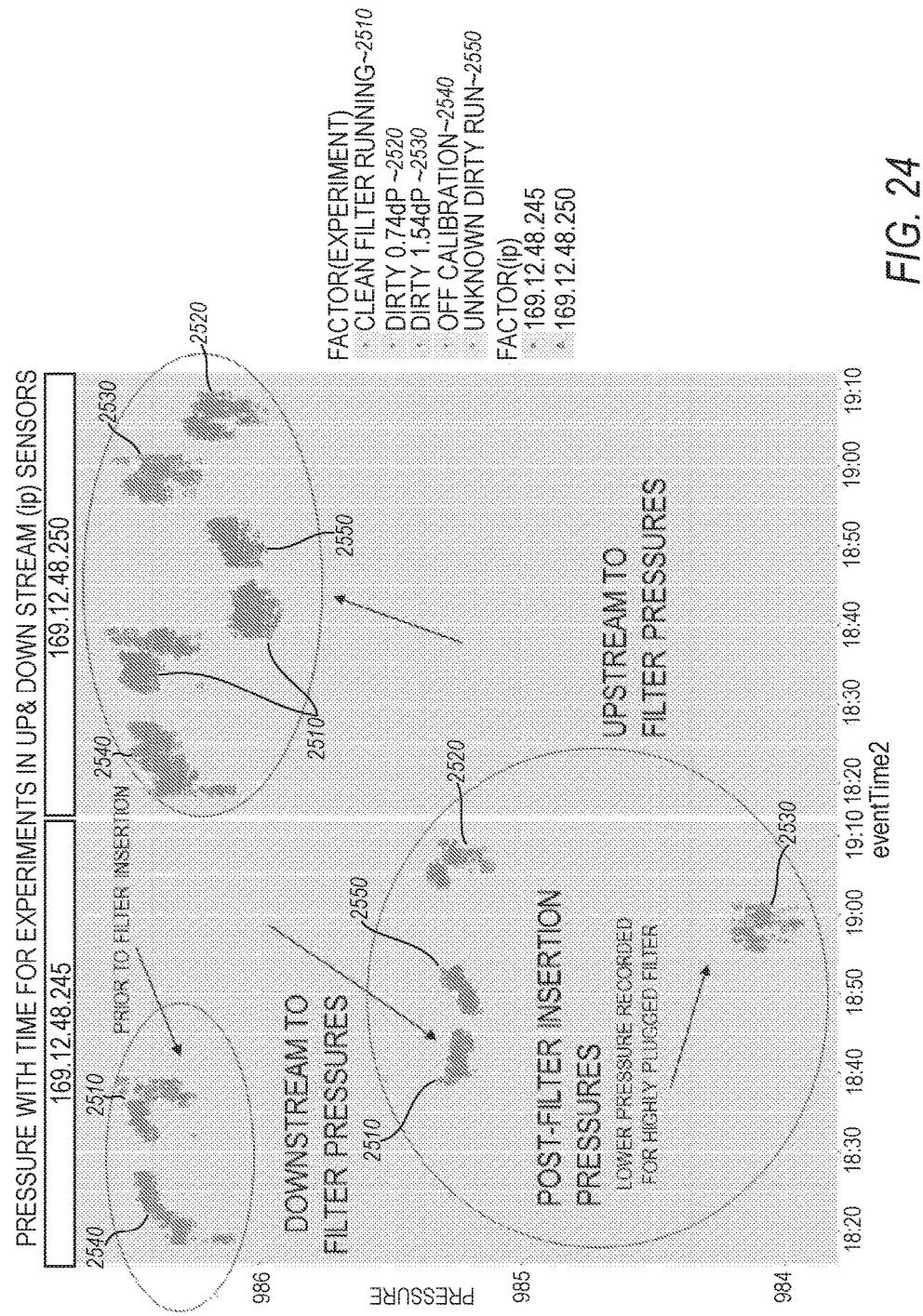
FIG. 24 illustrates multiple pressure measurements indicative of differential pressure across a filter under varying conditions over time according to an example embodiment.

FIG. 24 illustrates multiple pressure measurements indicative of differential pressure across a filter under varying conditions over time. A legend indicates various factors with reference numbers. The different states listed in the legend to the right (factor(experiment)) are as follows:

Cleanfilterrunning 2510—this is the furnace with the fan running with a new clean filter Dirty0.74dP 2520—an obstructed filter with the value of 0.74 inches of water Dirty1.54dP 2530—an obstructed filter with the value of 1.54 inches of water (more obstructed than 0.74)

Offcalibration 2540—the furnace is not running and the pressure is equalized in both chambers to atmospheric pressure Unknowndirtyrun 2550—an obstructed filter of unknown filtration level.

FIGS. 25, 26, 27, 28, 29, and 30 utilize a similar legend, with the first two digits of the reference numbers indicative of the figure number and the last two digits being the same as those in FIG. 24.

Figure 25:
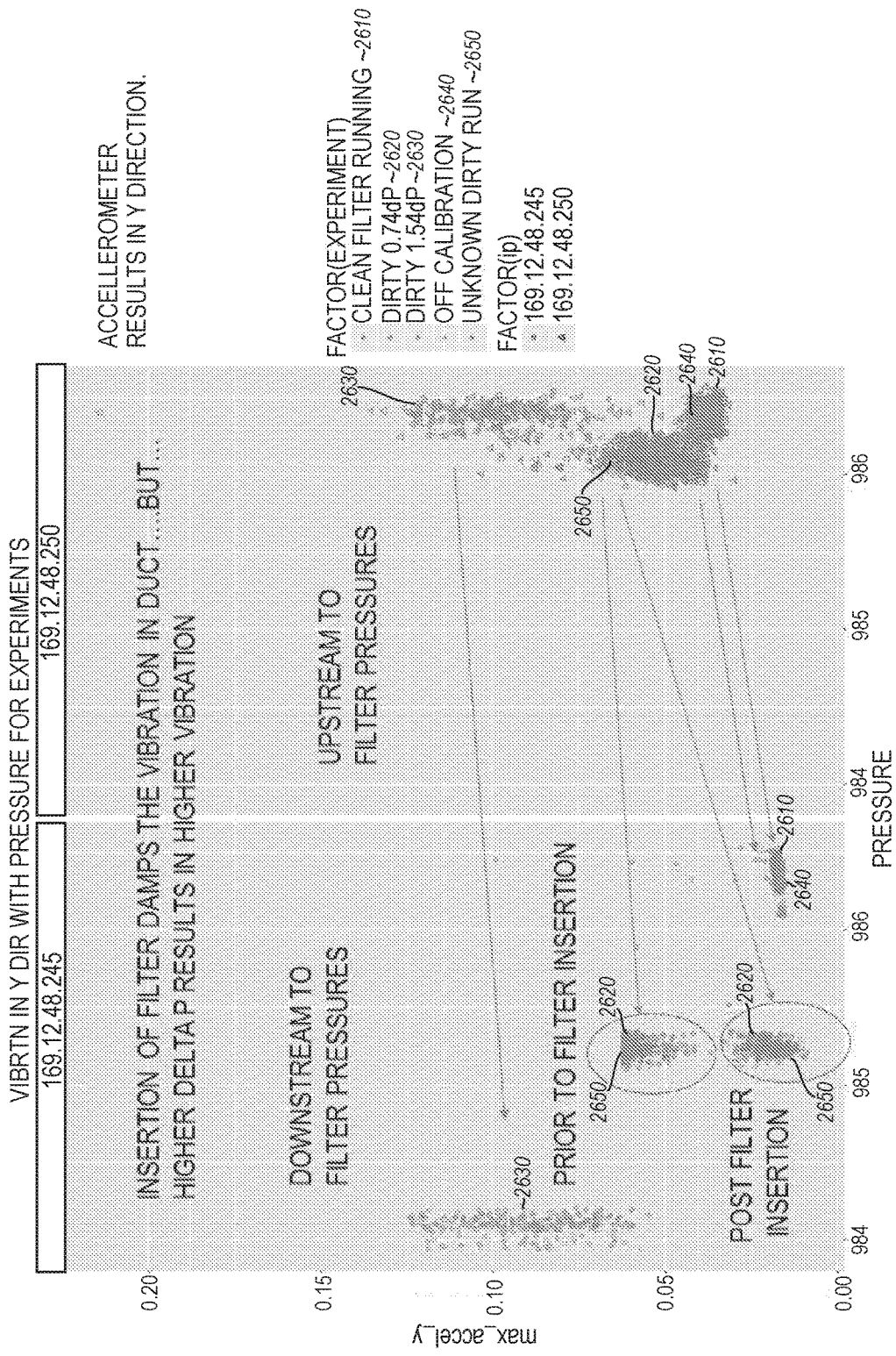
FIG. 25 illustrates data collected from an accelerometer sensor measuring vibration in a y-direction in the duct in which the filter is inserted according to an example embodiment.
Figure 26:
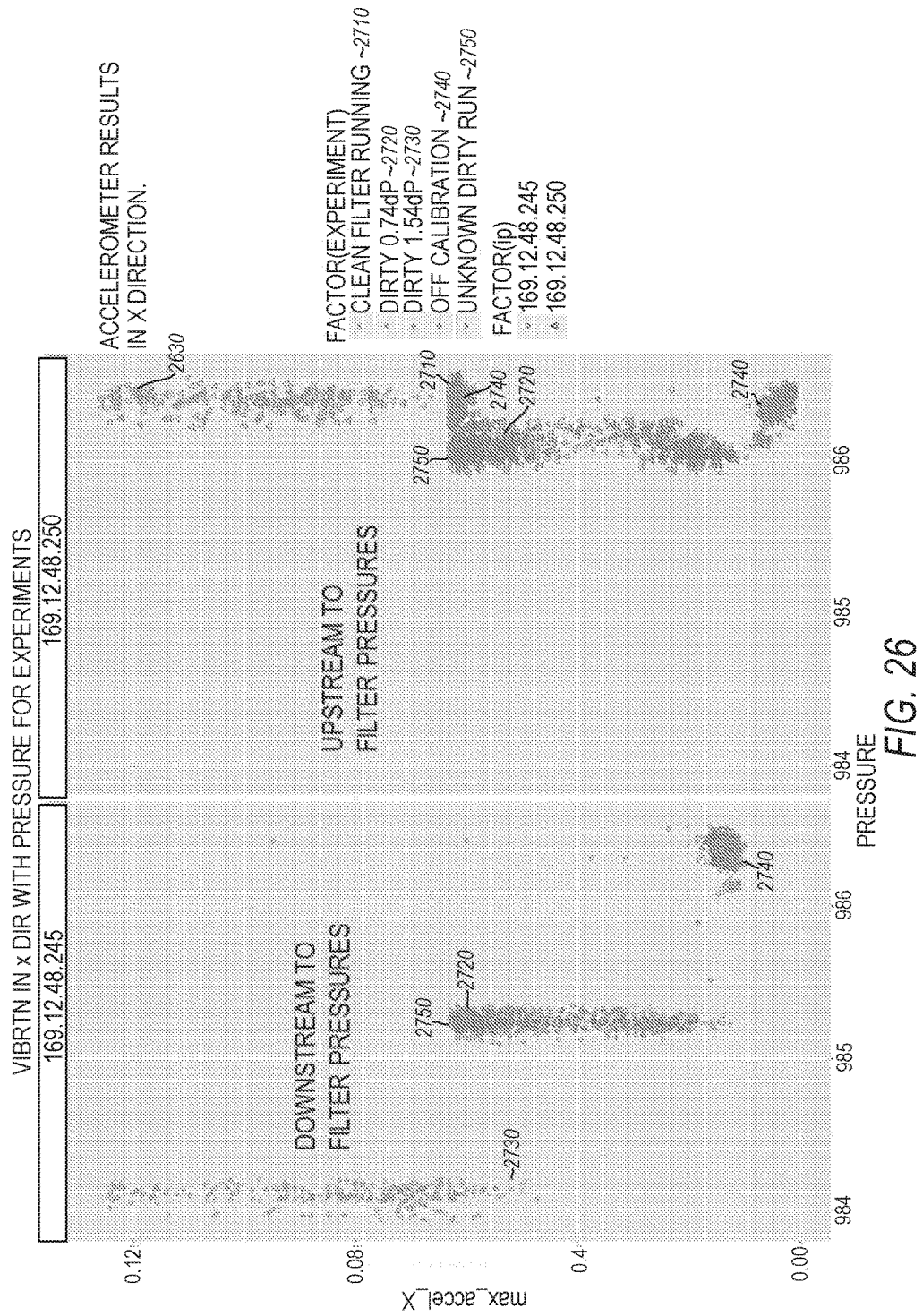
FIG. 26 similarly illustrates measurements of vibration in an x-direction according to an example embodiment.
Figure 27:
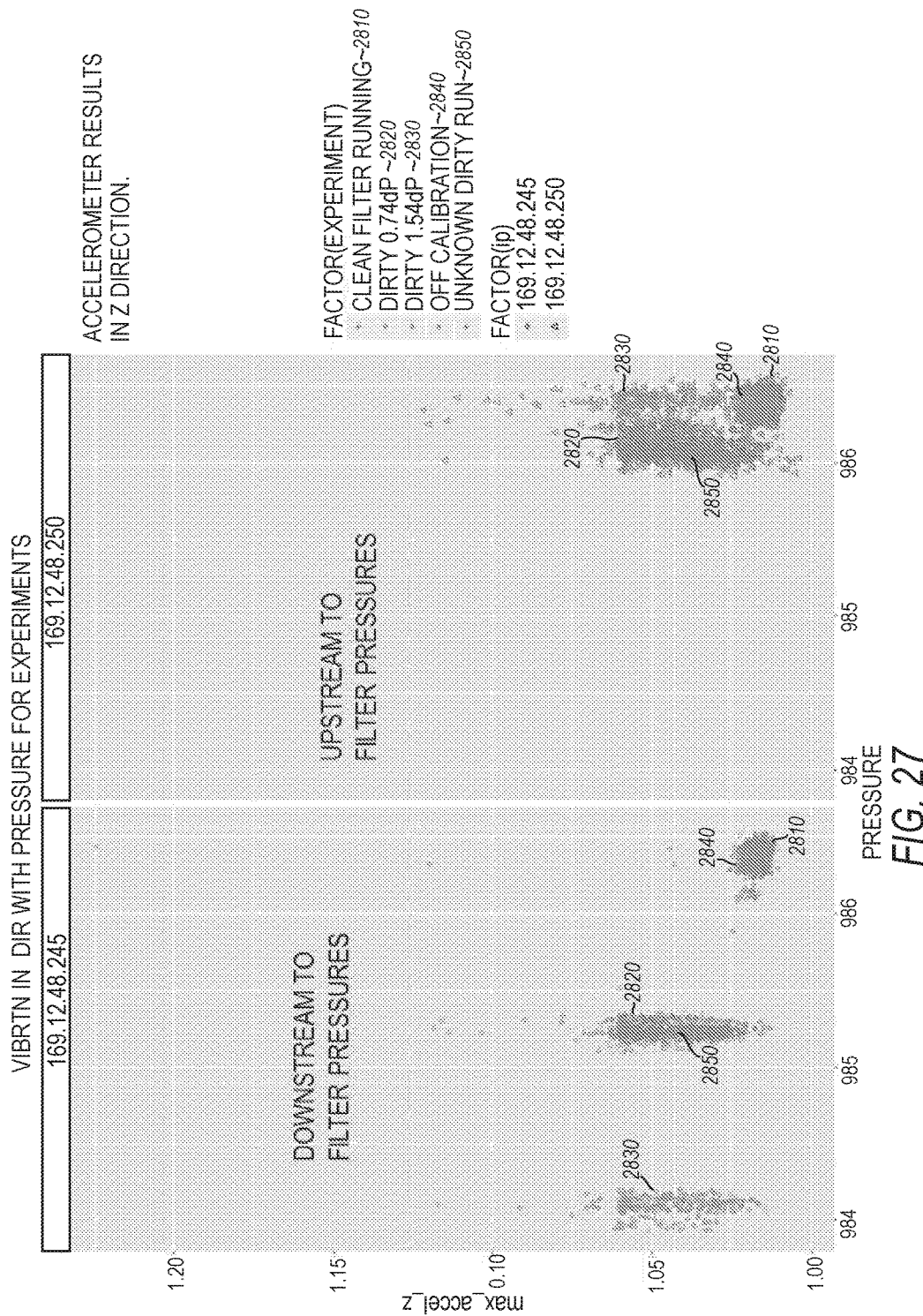
FIG. 27 similarly illustrates measurement of vibration in a z-direction according to an example embodiment.
Figure 28:
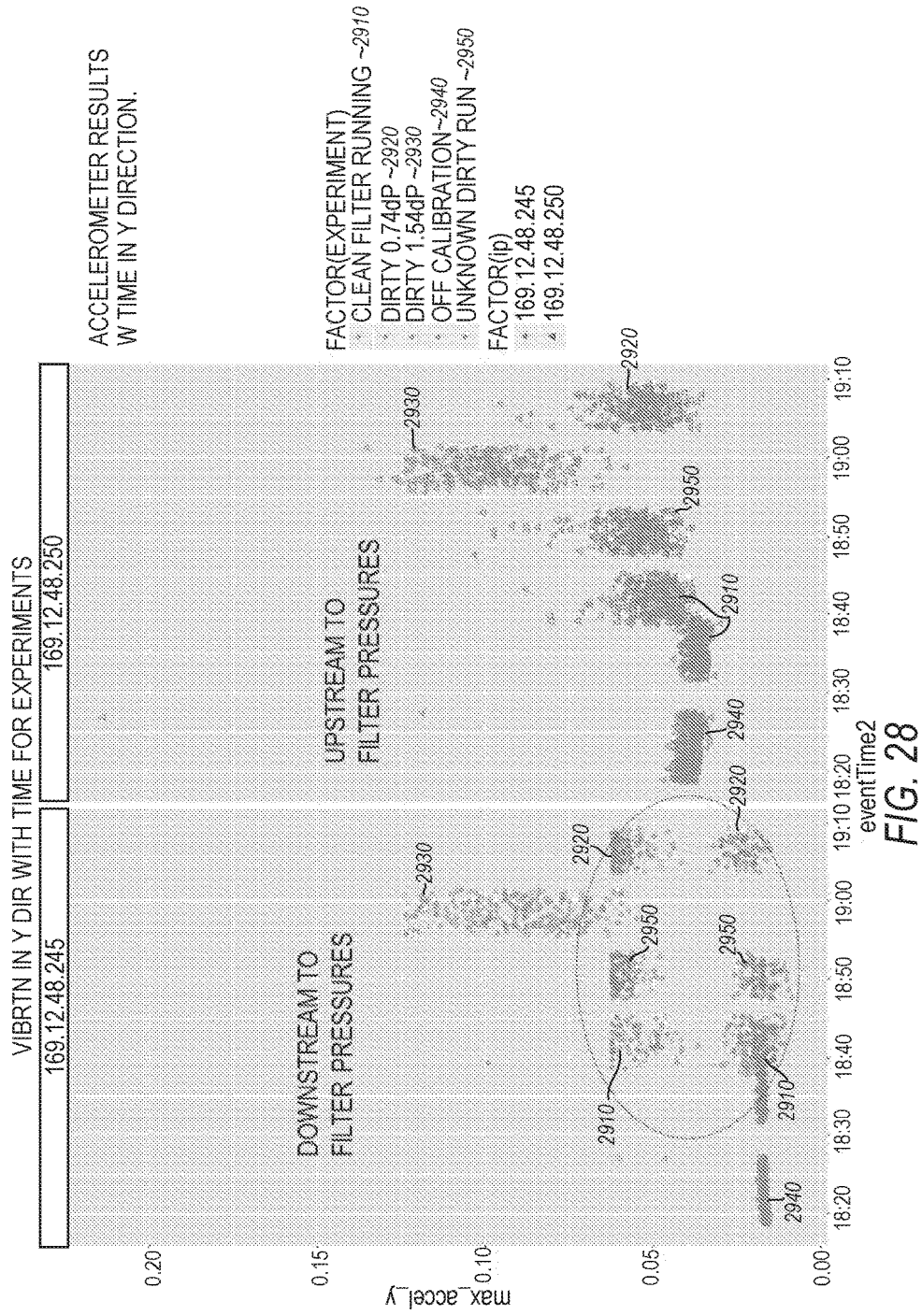
FIG. 28 illustrates accelerometer results with respect to time in the y-direction according to an example embodiment.
Figure 29:
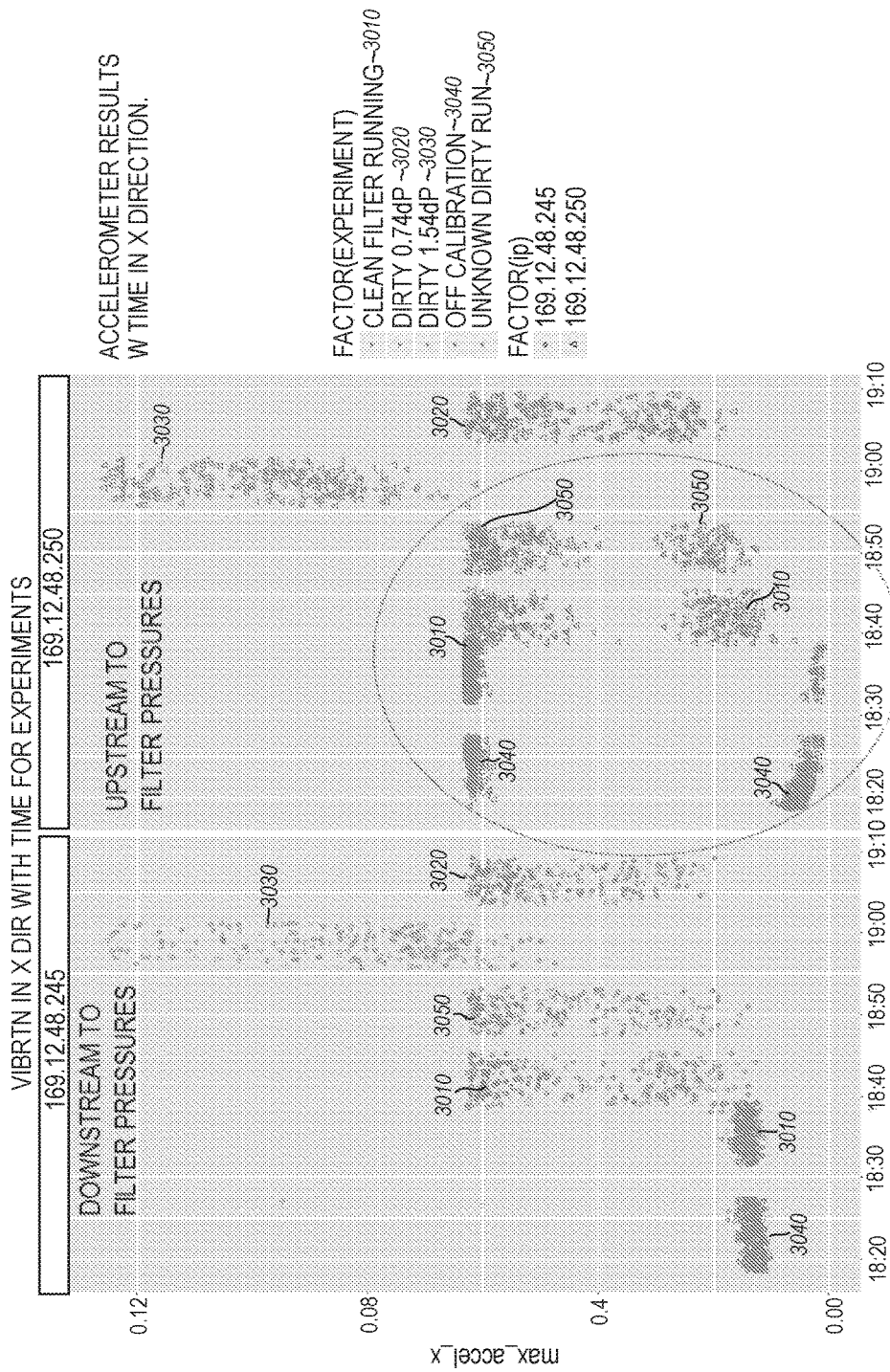
FIG. 29 illustrates accelerometer results with respect to time in the x-direction according to an example embodiment.
Figure 30:
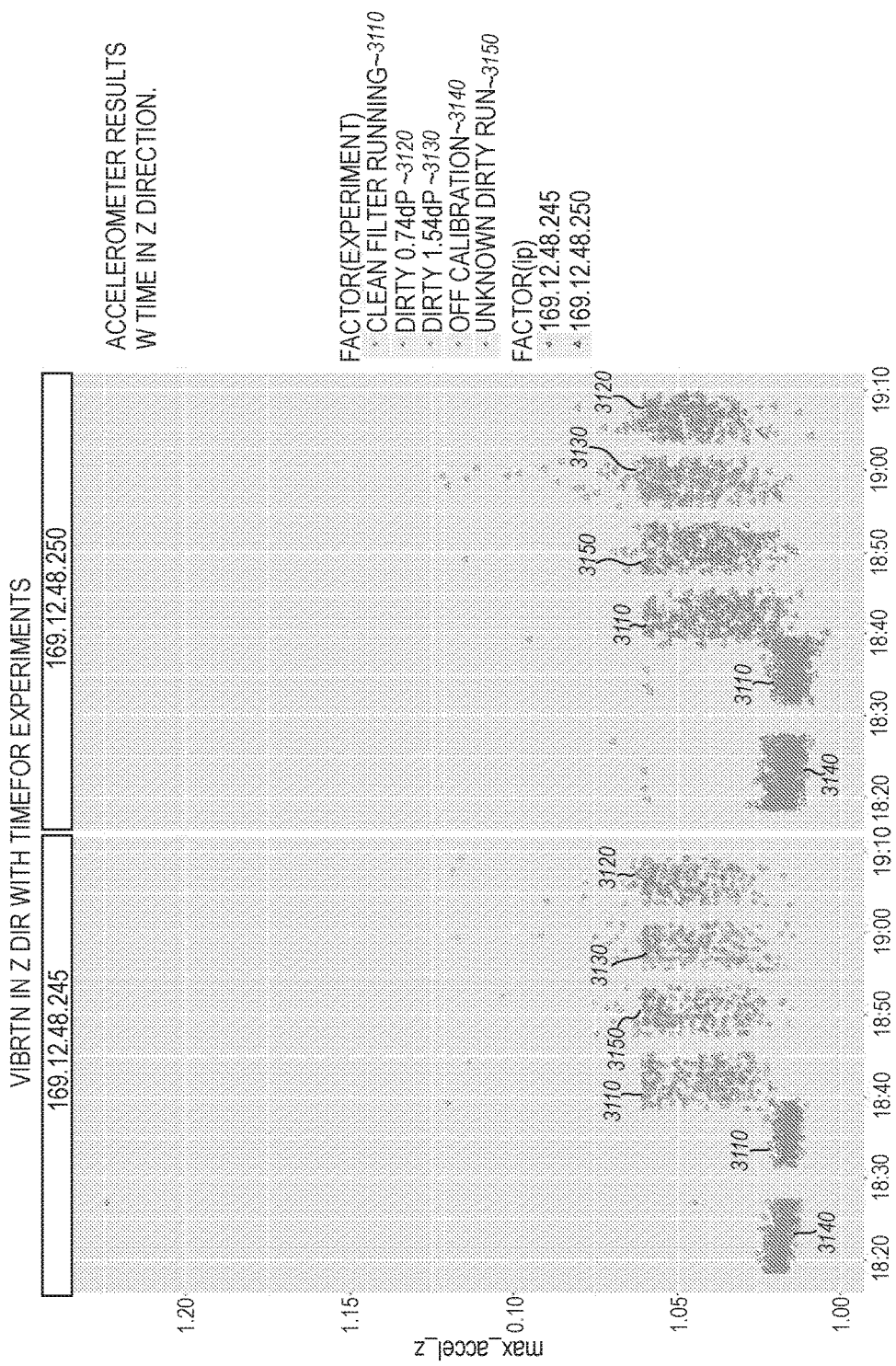
FIG. 30 illustrates accelerometer results with respect to time in the z-direction according to an example embodiment.

FIG. 25 illustrates data collected from an accelerometer sensor measuring vibration in a y-direction in the duct in which the filter is inserted. FIG. 26 similarly illustrates measurements of vibration in an x-direction. FIG. 27 similarly illustrates measurement of vibration in a z-direction. FIG. 28 illustrates accelerometer results with respect to time in the y-direction. FIG. 29 illustrates accelerometer results with respect to time in the x-direction. FIG. 30 illustrates accelerometer results with respect to time in the z-direction.

Note: Factor(ip) distinguishes TWO DIFFERENT SENSORS. 169.12.46.245 is DOWNSTREAM while 169.12.46.250 is UPSTREAM. The dirtier the filter, the greater the pressure drop downstream. The upstream sensors do not identify a significant pressure difference (right side of graph). These findings suggest that if a single pressure sensor is used, then the pressure sensor should typically be placed on the downstream side (after the filter).

The pressure differential is created by the suction between the obstructed filter and the fan drawing air.

$P_1$=Upstream Sensor Pressure $P_2$=Downstream Sensor Pressure $\Delta = P_1 - P_2$=Pressure Difference between Upstream Sensor Pressure and Downstream Sensor Pressure T=Time A single sensor can work downstream (after the filter) and the system may be aware of time as well as a state of the furnace to assist in sensor performance. The state can be determined through accelerometer information to identify whether or not the furnace is running, or alternatively the state may be inferred by a temporal analysis of the pressure measurements. Simply separating high and low readings and averaging them may clearly identify which measurements correspond to the state of the furnace. Determining the pressure when the furnace is off may be useful in determining the baseline for the current barometric pressure. In one embodiment, determining the filter condition from a single sensor includes obtaining time-based pressure data points from the sensor; calculating a mean difference between obtained adjacent pressure data points; and estimating filter life based on the identification of a pressure difference in adjacent points that is greater than a threshold pressure difference.

Figure 31:
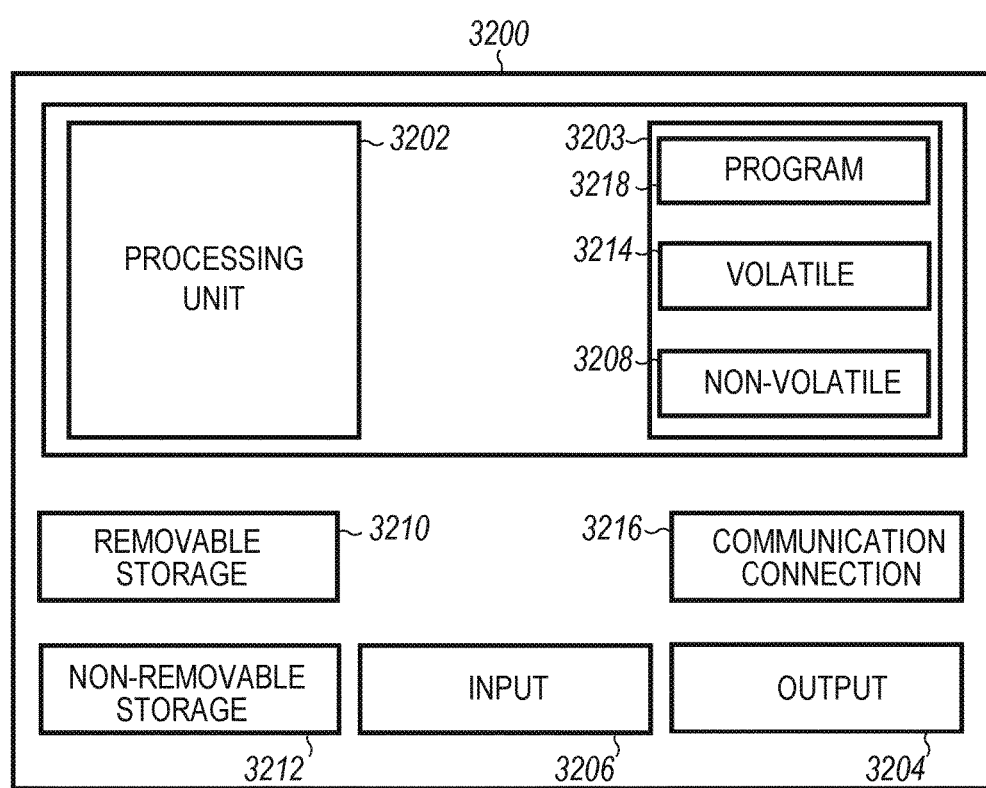
FIG. 31 is a block schematic diagram of a computer system to implement circuitry and methods according to an example embodiment.

FIG. 31 is a block schematic diagram of a computer system 3200 to implement methods according to example embodiments, such as implementation of smart filter circuitry and communications and implementation of a mobile device. All components need not be used in various embodiments.

One example computing device in the form of a computer 3200, may include a processing unit 3202, memory 3203, removable storage 3210, and non-removable storage 3212. Although the example computing device is illustrated and described as computer 3200, the computing device may be in different forms in different embodiments. For example, the computing device may instead be a smartphone, a tablet, smartwatch, or other computing device including the same or similar elements as illustrated and described with regard to FIG. 32. Devices such as smartphones, tablets, and smartwatches are generally collectively referred to as mobile devices. Further, although the various data storage elements are illustrated as part of the computer 3200, the storage may also or alternatively include cloud-based storage accessible via a network, such as the Internet.

Memory 3203 may include volatile memory 3214 and non-volatile memory 3208. Computer 3200 may include—or have access to a computing environment that includes—a variety of computer-readable media, such as volatile memory 3214 and non-volatile memory 3208, removable storage 3210 and non-removable storage 3212. Computer storage includes random access memory (RAM), read only memory (ROM), erasable programmable read-only memory (EPROM) & electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices capable of storing computer-readable instructions for execution to perform functions described herein.

Computer 3200 may include or have access to a computing environment that includes input 3206, output 3204, and a communication connection 3216. Output 3204 may include a display device, such as a touchscreen, that also may serve as an input device. The input 3206 may include one or more of a touchscreen, touchpad, mouse, keyboard, camera, one or more device-specific buttons, one or more sensors integrated within or coupled via wired or wireless data connections to the computer 3200, and other input devices. The computer may operate in a networked environment using a communication connection to connect to one or more remote computers, such as database servers, including cloud based servers and storage. The remote computer may include a personal computer (PC), server, router, network PC, a peer device or other common network node, or the like. The communication connection may include a Local Area Network (LAN), a Wide Area Network (WAN), cellular, Wi-Fi, Bluetooth, or other networks.

Computer-readable instructions stored on a computer-readable storage device are executable by the processing unit 3202 of the computer 3200. A hard drive, CD-ROM, and RAM are some examples of articles including a non-transitory computer-readable medium such as a storage device. The terms computer-readable medium and storage device do not include carrier waves.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

EMBODIMENTS

1. An air filter comprising: filter media; a sensor; and circuitry coupled to the sensor, the circuitry configured to receive data from the sensor representative of the condition of the filter media and wirelessly transmit such data.

2. The air filter of embodiment 1 wherein the sensor comprises a pressure sensor.

3. The air filter of embodiment 2 wherein the pressure sensor is a differential pressure sensor positioned to be exposed to upstream pressure and downstream pressure with respect to the filter media while air is moved through the filter media.

4. The air filter of embodiment 3 wherein the differential pressure sensor comprises: a first opening and a second opening, wherein the second opening comprises a tube configured to extend from a downstream side of the filter media through the filter media to an upstream side of the filter media; and a nut adapted to attach to the tube on the upstream side of the filter media to retain the differential pressure sensor to the filter media.

5. The air filter of any of embodiments 2-4 wherein the pressure sensor is an absolute pressure sensor supported on a downstream side of the filter media to measure downstream pressure while air is moved through the filter media.

6. The air filter of embodiment 5 wherein the circuitry is adapted to determine a pressure difference across the filter media as a function of the data from the absolute pressure sensor.

7. The air filter of embodiment 5 and further comprising a second sensor to provide second data, wherein the circuitry is further adapted to combine the second data with the data from the pressure sensor to determine the pressure difference.

8. The air filter of embodiment 7 wherein the second sensor comprises at least one sensor configured to sense operation of a fan to move air through the filter material.

9. The air filter of embodiment 7 wherein the second sensor is selected from the group consisting of a strain gage sensor, vibration sensor, hot wire airflow sensor, strain gage airflow sensor, and vane airflow sensor.

10. The air filter of any of embodiments 1-9 wherein the sensor comprises one or more sensors selected from the group consisting of absolute pressure sensor, differential pressure sensor, strain gage sensor, optical sensor, vibration sensor, hot wire airflow sensor, strain gage airflow sensor, vane airflow sensor, and air quality sensor.

11. The air filter of any of embodiments 1-10 and further comprising an electronically readable filter ID, wherein the circuitry is further adapted to read the filter ID and transmit the filter ID.

12. The air filter of any of embodiments 1-11 wherein the circuitry is further adapted to generate an alert indicative of a time to replace the air filter as a function of the sensed condition of the filter.

13. The air filter of any of embodiments 1-12 wherein the circuitry wirelessly transmits data by at least one communication protocol selected from the group consisting of Bluetooth, Bluetooth Low Energy, ZigBee, Zwave, and Wi-Fi.

14. A device comprising: a processor; a display coupled to the processor; and a memory device coupled to the processor and having a program stored thereon for execution by the processor to perform operations comprising: wirelessly receiving data from a sensor representative of the condition of filter media of an air filter having air flowing therethrough; providing a visual indication to a user on the display representative of the condition of the filter media as a function of the received data.

15. The device of embodiment 14 wherein the operations further comprising providing an option to a user of the device to order a replacement filter.

16. The device of any of embodiments 14-15 wherein the visual indication comprises a graph representative of condition of the filter media over time, including a remaining period of useful life of the filter media.

17. The device of any of embodiments 14-16 wherein the visual indication is provided as a function of user profile information indicative of air quality.

18. The device of embodiment 17 wherein the user profile information is indicative of a medical condition correlated to air quality.

19. A method comprising: wirelessly receiving pressure information representative of a downstream pressure, the information received from a sensor associated with an air filter; processing the pressure information to determine a difference in pressure between an upstream side of the air filter and the downstream side of the air filter; and generating an indication of a condition of the filter responsive to the difference in pressure.

20. The method of embodiment 19 wherein the pressure information comprises at least one pressure measurement while air is moving through the air filter and at least one pressure measurement while air is not moving through the air filter, and wherein the difference in pressure is determined from such pressure measurements.

21. The method of any of embodiments 19-20 wherein the pressure information comprises at least one pressure measurement from the upstream side of the air filter and at least one pressure measurement from the downstream side of the air filter.

22. A method comprising: wirelessly receiving information representative of a condition of an air filter positioned in a furnace duct; generating an indication of a condition of the filter responsive to the received information; and wirelessly transmitting data representative of the indication of the condition of the filter to a device for display of the indication to a user.

23. A method comprising: sensing a condition of air filter media; and wirelessly transmitting information representative of the condition of the air filter media such that the information is receivable by an end user.

24. The air filter of any of embodiments 1-13 and further comprising means for coupling the sensor to the filter media in a manner permitting removal and reuse of the sensor with replacement filter media.

25. The air filter of any of embodiments 1-13 and further comprising: a frame to hold the filter media; and means for coupling the sensor to the frame.

26. The air filter of embodiment 25 wherein the filter media is replaceable in the frame.

27. The device of any of embodiments 14-18 wherein the operations further comprise: obtaining information from the filter; and using the information to enable or disable providing the visual indication to the user.

28. The device of any of embodiments 14-18 and 27 wherein the operations further comprise: obtaining information from the filter; and wherein providing a visual indication to a user on the display representative of the condition of the filter media as a function of the received data is a function of a threshold set based on the obtained information.

29. The device or method of any of the previous embodiments, wherein the circuitry wirelessly transmits data by at least one communication protocol selected from the group consisting of Bluetooth, Bluetooth Low Energy, ZigBee, Zwave, and Wi-Fi.

30. The device or method of embodiment 29, wherein the circuitry transmits data to a mobile device, and wherein the mobile device, via one or more processors, is adapted to generate an alert indicative of a time to replace the air filter as a function of the sensed condition of the filter.

31. The device of method of any of the previous embodiments, and wherein the sensor is releasably coupled to the filter media.

The following statements are potential claims that may be converted to claims in a future application. No modification of the following statements should be allowed to affect the interpretation of claims which may be drafted when this provisional application is converted into a regular utility application.

The invention claimed is:

1. An air filter comprising:
   filter media comprising a downstream side and an upstream side;
   an absolute pressure sensor attached to the downstream side of the filter media adapted to measure downstream pressure while air is moved through the filter media; and
   circuitry coupled to the sensor, the circuitry configured to receive pressure data from the sensor representative of the condition of the filter media and wirelessly transmit such data, wherein the sensor does not rely on the monitoring of airflow through a bypass through or around the filter media.

2. The air filter of claim 1, wherein the circuitry is adapted to transmit sensor data to a memory device coupled to a processor and having a program stored thereon for execution by the processor to determine a pressure at the filter media as a function of the data from the pressure sensor.

3. The air filter of claim 2, wherein the processor is programmed to determine a status of the filter by a temporal analysis of the pressure data.

4. The air filter of claim 1, wherein the circuitry or the processor is adapted to determine a pressure difference across the filter media.

5. The air filter of claim 1 and further comprising a second sensor to provide second data, wherein the circuitry is further adapted to combine the second data with the data from the pressure sensor to determine a pressure or pressure difference.

6. The air filter of claim 1 and further comprising a perimeter frame.

7. The air filter of claim 6, wherein the filter media is pleated, and wherein the frame has a generally rectangular shape.

8. The air filter of claim 1 and further comprising an electronically readable filter ID, wherein the circuitry is further adapted to at least one of read the filter ID and transmit the filter ID.

9. The air filter of claim 8, wherein the circuitry is adapted to use the filter ID to enable or disable providing wireless data transmission.

10. The air filter of claim 1, wherein the circuitry is adapted to either transmit data intermittently, acquire data intermittently, or both.

11. The air filter of claim 1, wherein the circuitry is further adapted to generate an alert indicative of a time to replace the air filter as a function of the sensed condition of the filter.

12. The air filter of claim 1, wherein the circuitry is co-located with the sensor in a sensor housing.

13. The air filter of claim 1, wherein the circuitry wirelessly transmits data by at least one communication protocol selected from the group consisting of Bluetooth and Bluetooth Low Energy.

14. The air filter of claim 1, wherein the sensor comprises a single sensor attached to only the downstream side of the filter media.

15. A system for determining the useful life of an air filter, the system comprising:
   filter media comprising a downstream side and an upstream side; a single sensor attached to only the downstream side of the filter media for sensing a condition of the filter; and circuitry coupled to the sensor, the circuitry configured to receive data from the sensor representative of the condition of the filter media and wirelessly transmit such data; and
   a personal mobile device comprising a processor; a display coupled to the processor; and a memory device coupled to the processor and having a program stored thereon for execution by the processor to perform operations comprising: wirelessly receiving data directly or indirectly from the sensor representative of a condition of filter media; providing a visual indication to a user on the display representative of the condition of the filter media as a function of the received data, wherein the visual indication includes a graphical representation of a remaining period of useful life of the filter media, and wherein the operations further comprise generating a filter type recommendation based on user profile information indicative of air quality.

16. The system of claim 15, wherein the circuitry is co-located with the sensor in a sensor housing.

17. The system of claim 15, wherein the operations further comprise obtaining time-based pressure data points from the sensor; calculating a mean difference between obtained adjacent pressure data points; and estimating filter life based on the identification of a pressure difference in adjacent points that is greater than a threshold pressure difference.

18. The system of claim 15, wherein the user profile information is indicative of a medical condition correlated to air quality.

19. The system of claim 15, wherein the visual indication is provided as a function of user profile information indicative of air quality.

20. A system for determining the useful life of an air filter, the system comprising:

An air filter comprising: filter media comprising a downstream side and an upstream side;
  an absolute pressure sensor attached to the downstream side of the filter media adapted to measure downstream pressure while air is moved through the filter media; and
  circuitry coupled to the sensor, the circuitry configured to receive pressure data from the sensor representative of the condition of the filter media and wirelessly transmit such data, wherein the sensor does not rely on the monitoring of airflow through a bypass through or around the filter media; and a personal mobile device comprising a processor; a display coupled to the processor; and a memory device coupled to the processor and having a program stored thereon for execution by the processor to perform operations comprising: wirelessly receiving data directly or indirectly from the sensor representative of a condition of filter media; providing a visual indication to a user on the display representative of the condition of the filter media as a function of the received data, wherein the visual indication includes a graphical representation of a remaining period of useful life of the filter media.

21. The system of claim 20, wherein the operations further comprise generating a filter type recommendation based on user profile information indicative of air quality.

* * * * *

UNITED STATES PATENT AND TRADEMARK OFFICE
CERTIFICATE OF CORRECTION

PATENT NO.         : 10,363,509 B2                                      Page 1 of 1
APPLICATION NO.    : 15/876742
DATED              : July 30, 2019
INVENTOR(S)        : Jonathan Arthur It is certified that error appears in the above-identified patent and that said Letters Patent is hereby corrected as shown below:

In the Drawings

Figure 24, Line 1, delete "UP&" and insert -- UP & --

Figure 25, Line 3, delete "ACCELLEROMETE" and insert -- ACCELEROMETER --

Figure 30, Line 1, delete "TIMEFOR" and insert -- TIME FOR --

In the Specification

Column 7, Line 19, delete "miming" and insert -- running --

Column 18, Line 5, delete "$\Delta = P_1\_P_2=$" and insert -- $\Delta = P_1 - P_2 =$ --

In the Claims

Column 23, Line 11, delete "An" and insert -- an --

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*